US012661253B2

(12) United States Patent
Harmer et al.

(10) Patent No.: US 12,661,253 B2
(45) Date of Patent: Jun. 23, 2026

(54) HYPERTHERMIA IMPLANTS AND A METHOD AND SYSTEM FOR HEATING THE IMPLANT

(71) Applicant: ENDOMAGNETICS LIMITED, Cambridge (GB)

(72) Inventors: Quentin John Harmer, Cambridge (GB); Tiziano Agostinelli, Cambridge (GB); Kevin Lorimer, Cambridge (GB)

(73) Assignee: ENDOMAGNETICS LIMITED (GB)

( * ) Notice: Subject to any disclaimer, the term of this patent is extended or adjusted under 35 U.S.C. 154(b) by 1121 days.

(21) Appl. No.: 17/620,531

(22) PCT Filed: Jun. 25, 2020

(86) PCT No.: PCT/IB2020/056013
§ 371 (c)(1),
(2) Date: Dec. 17, 2021

(87) PCT Pub. No.: WO2020/261169
PCT Pub. Date: Dec. 30, 2020

(65) Prior Publication Data
US 2022/0313476 A1 Oct. 6, 2022

(30) Foreign Application Priority Data

Jun. 25, 2019 (GB) ...................................... 1909119

(51) Int. Cl.
*A61F 7/00* (2006.01)
*A61N 2/00* (2006.01)
*A61N 2/02* (2006.01)

(52) U.S. Cl.
CPC ................ *A61F 7/00* (2013.01); *A61N 2/004* (2013.01); *A61N 2/02* (2013.01); *A61F 2007/009* (2013.01); *A61F 2007/0096* (2013.01)

(58) Field of Classification Search
CPC ............... H01F 1/0304; H01F 1/15391; A61N 1/403–406
See application file for complete search history.

(56) References Cited

U.S. PATENT DOCUMENTS

| | | | |
|---|---|---|---|
| 4,660,025 A | 4/1987 | Humphrey | |
| 5,801,630 A | 9/1998 | Ho et al. | |

(Continued)

FOREIGN PATENT DOCUMENTS

| | | |
|---|---|---|
| CN | 109803576 A | 5/2019 |
| EP | 0710923 A2 | 5/1996 |

(Continued)

OTHER PUBLICATIONS

Translation of Chinese Office Action for Chinese application No. 202080046247.0 issued May 9, 2024 (9 pages).

(Continued)

*Primary Examiner* — Thaddeus B Cox
(74) *Attorney, Agent, or Firm* — K&L GATES LLP

(57) ABSTRACT

A hyperthermia implant 20 for hyperthermia treatment of tissue 30 of a human or animal body. The implant comprises at least one piece of a large Barkhausen jump material (LBJ) and a magnetic field may be applied to the implant to heat the surrounding tissue. The implant may also be deployed to mark a tissue site in the body for subsequent surgery, thereby providing a combined system for locating an implant and treating the surrounding area. The system includes a hand-held probe 14 to excite the implant below the switching field for bistable switching causing a harmonic response to be generated in a sub-bistable mode that allows the implant to be detected and localised.

20 Claims, 14 Drawing Sheets

(56) References Cited

U.S. PATENT DOCUMENTS

| | | | |
|---|---|---|---|
| 6,230,038 B1 | 5/2001 | von Gutfeld et al. | |
| 6,337,627 B1 | 1/2002 | von Gutfeld et al. | |
| 6,992,477 B2 | 1/2006 | Govari | |
| 10,595,957 B2 | 3/2020 | Mayes et al. | |
| 2003/0052785 A1 | 3/2003 | Gisselberg et al. | |
| 2010/0259251 A1* | 10/2010 | Boeve ................. | A61B 5/0515 |
| | | | 324/228 |

FOREIGN PATENT DOCUMENTS

| | | |
|---|---|---|
| EP | 0961301 A1 | 12/1999 |
| EP | 1258538 A1 | 11/2002 |
| EP | 1266614 A1 | 12/2002 |
| JP | 2003308576 | 10/2003 |
| JP | 2011-149906 | 8/2011 |
| JP | 2011-251042 | 12/2011 |
| WO | 2016/193753 A2 | 12/2016 |
| WO | 2018013935 A1 | 1/2018 |
| WO | 2019/180580 A1 | 9/2019 |

OTHER PUBLICATIONS

English translation of Japanese Office Action issued for Japanese Patent Application No. 2021-576328; date of drafting Feb. 20, 2024; (6 pages).

Ajay Kumar Gupta, et al.; "Synthesis and surface engineering of iron oxide nonparticles for biomedical applications"; Biomaterials; 26; (2005); pp. 3995-4021.

R.J. von Gutfeld, et al.; "Amorphous magnetic wires for medical locator applications"; Applied Physic Letters; Vo. 81; No. 10; (2002)' pp. 1913-1915.

PCT International Search Report and PCT Written Opinion for PCT International Patent Application No. PCT/IB2020/05613; mailing date Sep. 29, 2020; (15 pages).

Search Report under Section 17 for Great Britain Patent Application No. 1909119.8; date of search Jul. 24, 2019; (2 pages).

* cited by examiner

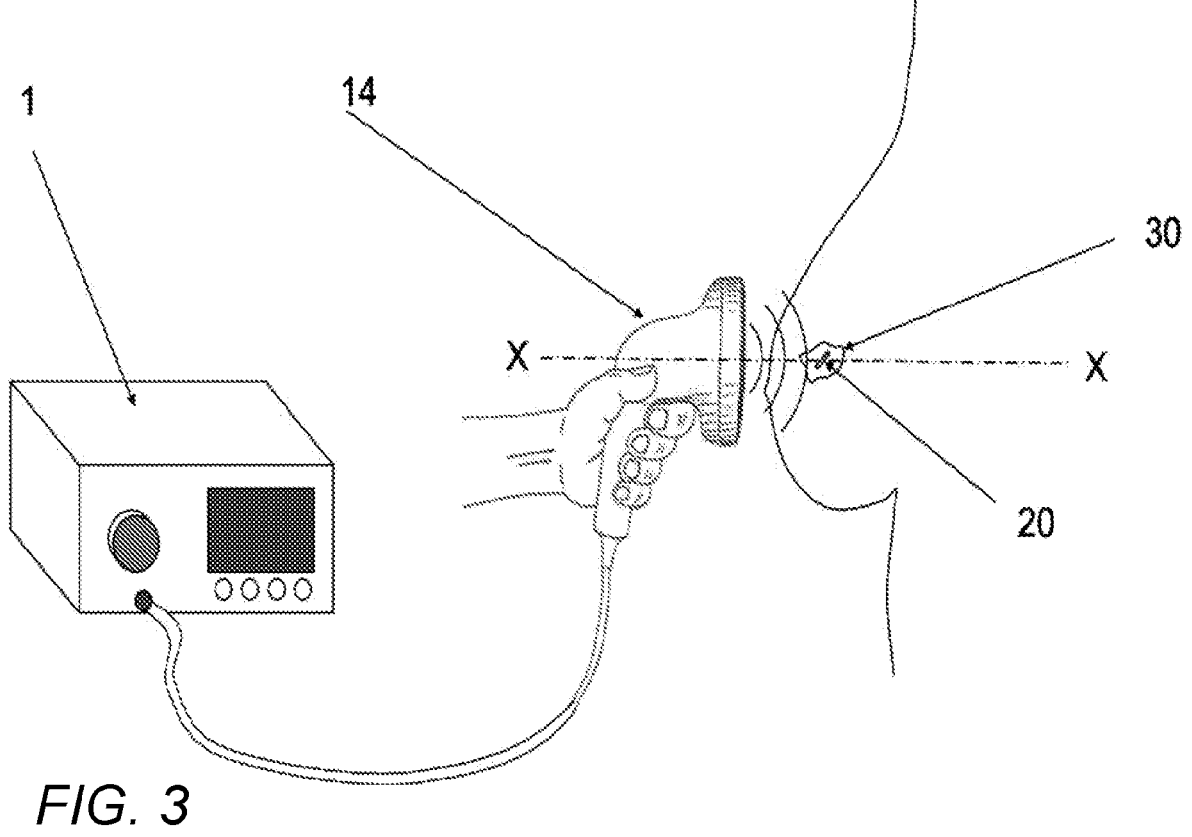
*FIG. 3*
*FIG. 4*
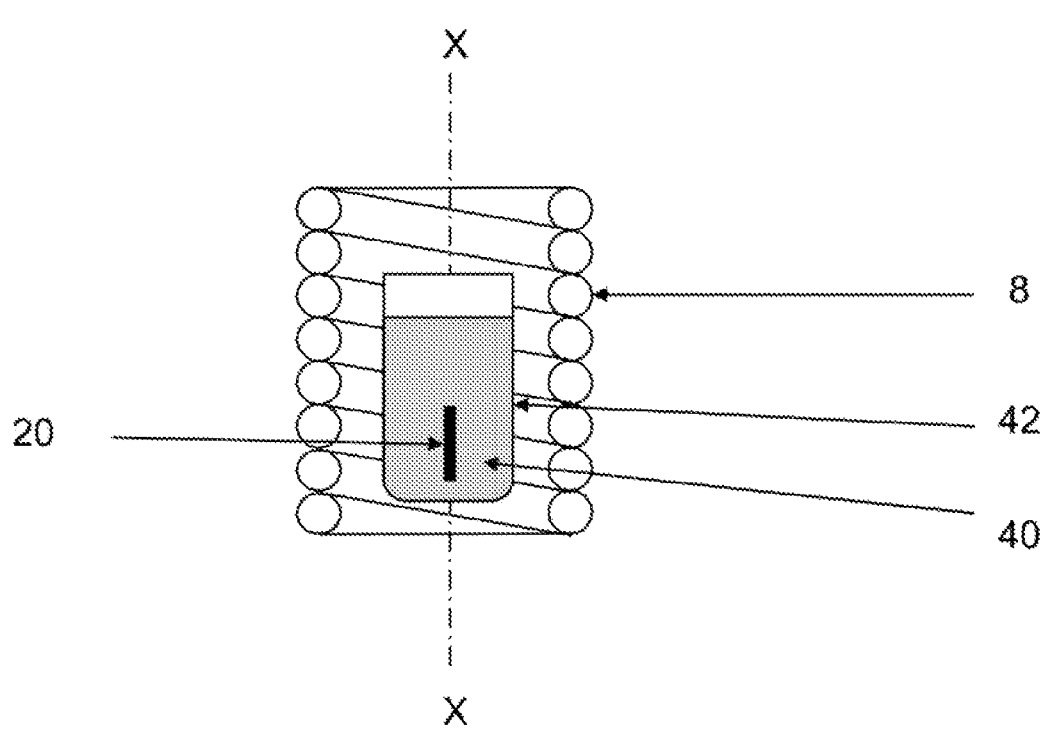

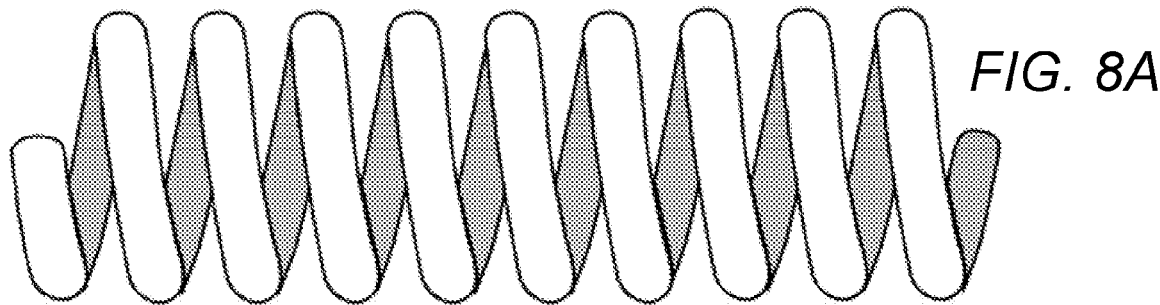
*FIG. 8A*
*FIG. 8B*
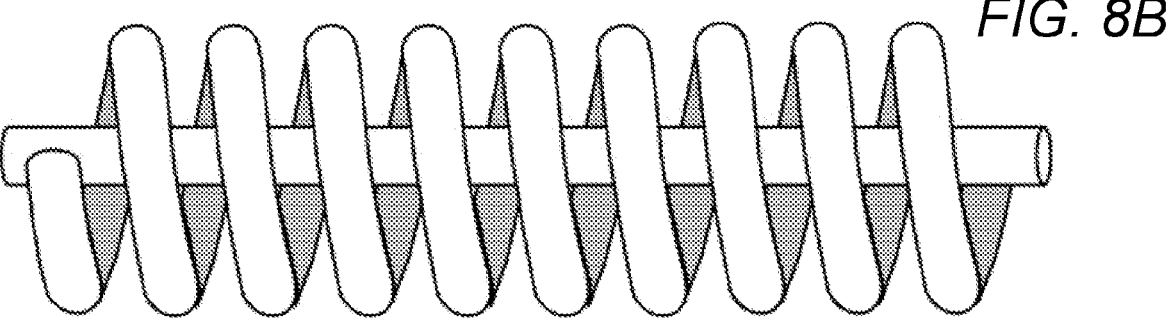

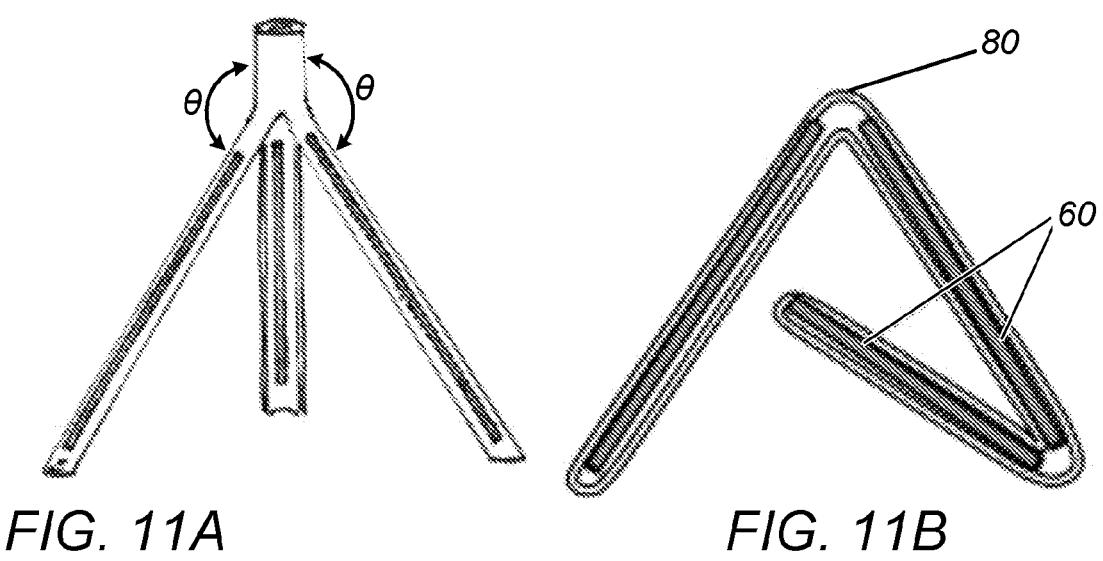
*FIG. 11A*
*FIG. 11B*
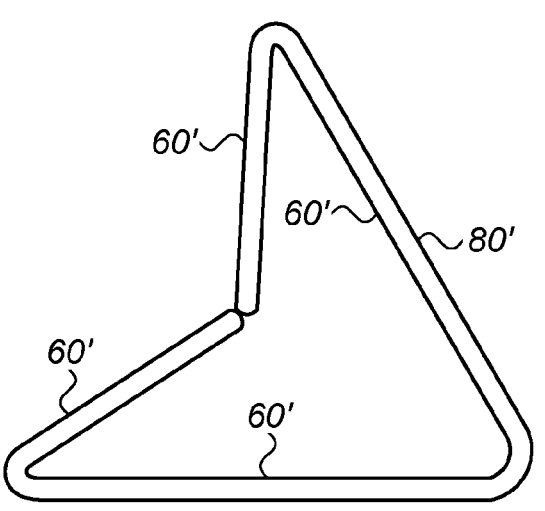
*FIG. 11C*

—— Ferritic stainless steel 0.9mm diameter x 5mm

--------- Amorphous high permeability microwire without LBJ, diameter 0.1mm x5.5mm — — — Three-side tetrahedron of amorphous microwire, 6mm side length. 0.33mm PET coating

*FIG. 14A*

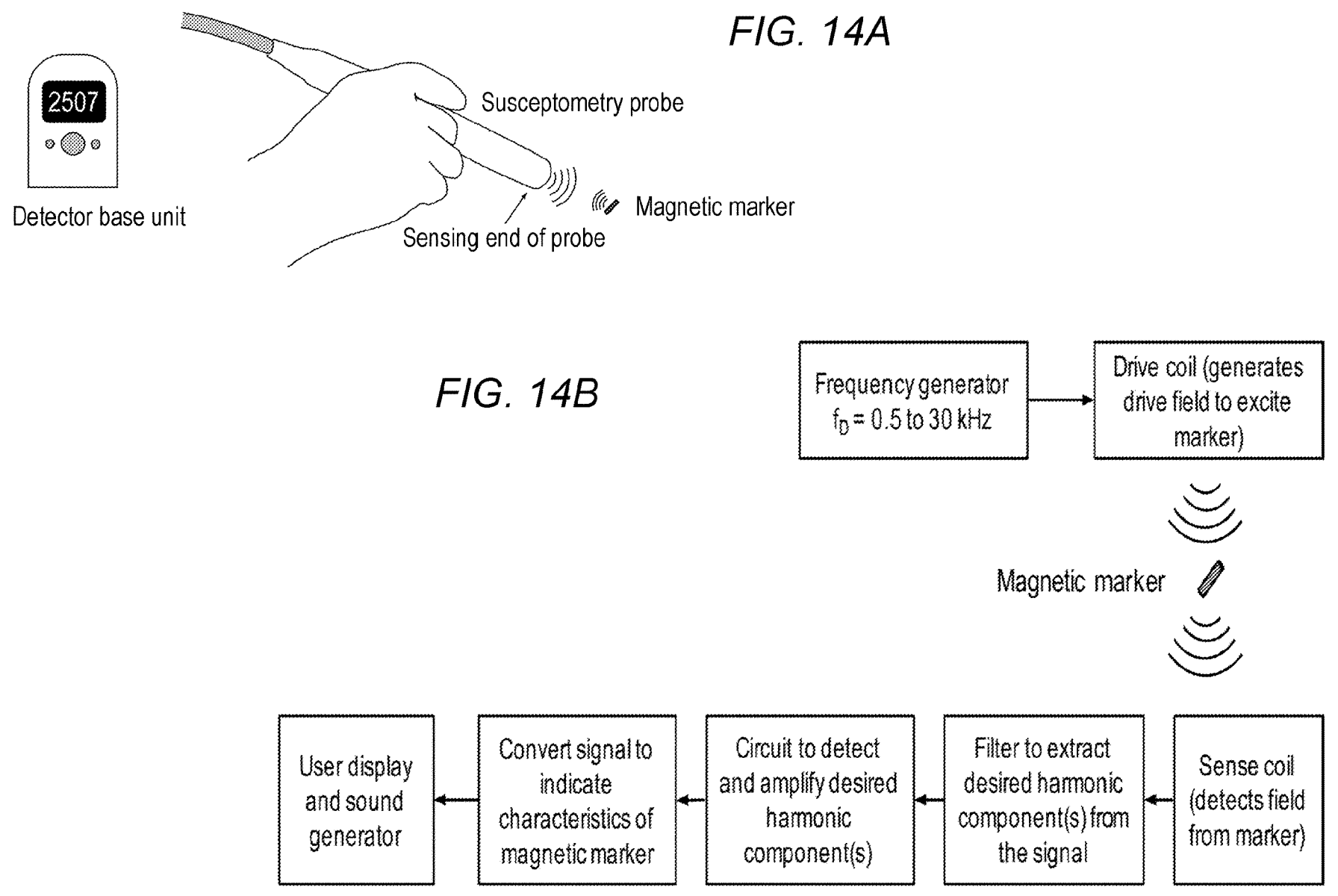

Susceptometry probe

Magnetic marker

Sensing end of probe

2507

Detector base unit

*FIG. 14B*

Frequency generator
$f_D$ = 0.5 to 30 kHz

Drive coil (generates drive field to excite marker)

Magnetic marker

Sense coil (detects field from marker)

Filter to extract desired harmonic component(s) from the signal

Circuit to detect and amplify desired harmonic component(s)

Convert signal to indicate characteristics of magnetic marker

User display and sound generator

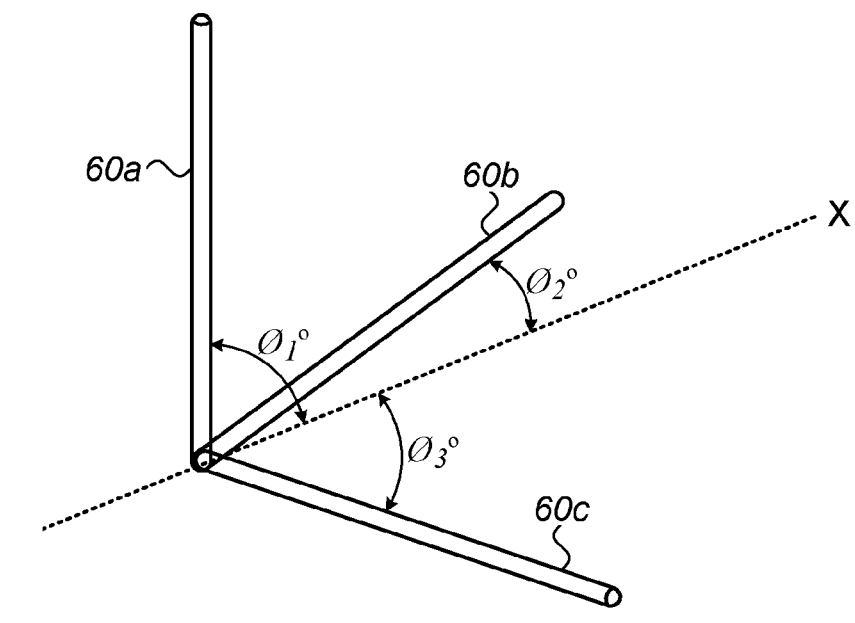
FIG. 16
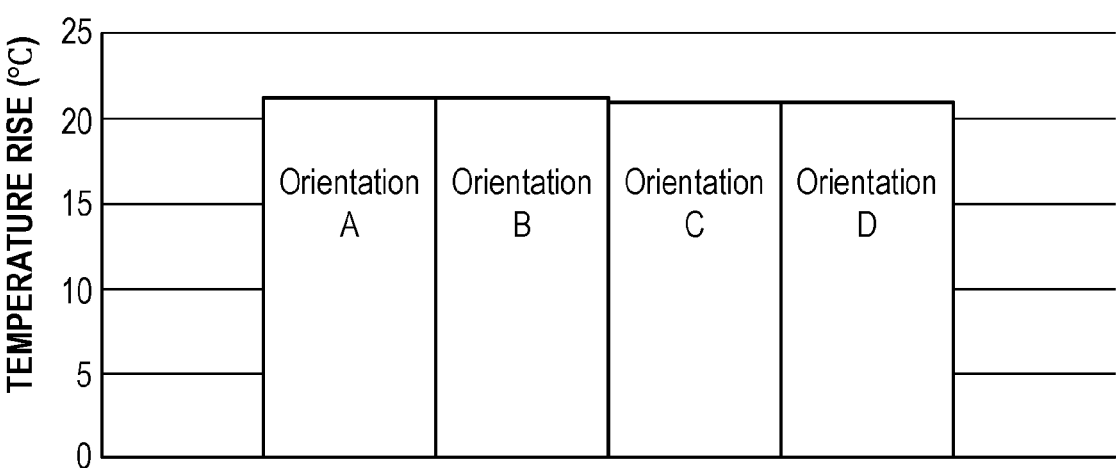
Four edged tetradedron. 4 pieces of 4.8mm lenth morphous microwire, Nitinol housing
   
FIG. 17

HYPERTHERMIA IMPLANTS AND A METHOD AND SYSTEM FOR HEATING THE IMPLANT

CROSS REFERENCE TO RELATED APPLICATIONS

This is the national phase under 35 U.S.C. § 371 of International Application No. PCT/IB2020/056013 filed on Jun. 15, 2020, which claims priority to and the benefit of Great Britain Patent Application No. 1909119.8 filed on Jun. 25, 2019, the entire disclosures of each of which are incorporated by reference herein.

FIELD OF THE INVENTION

This invention relates in general to the field of hyperthermia treatment of tissue, in particular the treatment of tumours using a hyperthermia implant.

BACKGROUND OF THE INVENTION

The traditional treatment for solid cancer tumours is surgical excision. However, for smaller tumours e.g. less than 20 mm and especially less than 10 mm it is desirable to avoid the trauma of a full surgical procedure under general anaesthetic, and more so for older or infirm patients. Many alternatives to surgical excision have been explored, including cryoablation, where the tissue is frozen, and hyperthermia, where the tissue is heated.

Two types of hyperthermia are known in the art, ablation hyperthermia where the tissue is heated sufficiently for the cells to be physically ablated and destroyed, and a gentler form of hyperthermia where the temperature of the tissue is raised to a level in the region of 42 to 45° C. at which point various cellular processes are activated that cause cells to die directly or enhance the ability of the immune system to recognise and kill the tumor cells. This gentler hyperthermia is also sometimes called 'adjuvant' hyperthermia because it enhances the effectiveness of other treatments such as chemotherapy, radiotherapy and immunotherapy, when used alongside them. Both approaches can be used to treat cancers.

Tumours treated with hyperthermia include breast, lung, liver, kidney, melanoma, and other solid tumour types. For successful hyperthermia the heat is preferably provided locally to the tumour in a controlled way and the heating of surrounding non-cancerous tissue is minimised.

An implant used for hyperthermia also needs to be convenient to deliver into the tissue. Typically, such an implant will be deployable through a narrow gauge needle e.g. 18 g to 14 g in order to reduce trauma to the patient. Ideally, such implants are less than 10 mm in length and preferably less than 6 mm in length prior to deployment so as to be unobtrusive, to minimise trauma during implantation, and to minimise unwanted heating of non-diseased tissue surrounding the tissue being treated. The hyperthermia implant may be placed during a biopsy or other surgical procedure at a site of interest in the body, for example a cancer lesion or lymph node. The implant is placed under imaging guidance such as ultrasound or X-ray/mammography. The implant should also be robust to be safely implanted without affecting its function.

An increasing proportion of cancer patients, especially breast cancer patients, are treated with chemotherapy (or other systemic therapy) prior to surgery or removal of the tumour, so called 'neo-adjuvant' therapy. The purpose of this is to shrink the tumour prior to surgery so that this is less invasive. In some cases this allows a breast conserving surgery where only a portion of the breast is removed, instead of removing the whole breast with a mastectomy. Typically, a marker is placed in the tumour or lymph node prior to neo-adjuvant therapy so that the tumour site can be located even if the tumour has been completely removed by the neo-adjuvant therapy. In the event that a tumour has shrunk to a sufficiently small size that hyperthermia therapy is suitable, a further hyperthermia implant would then need to be placed in the tumour or lymph node in order to treat it with hyperthermia. Most tumours are less than 20 mm at diagnosis and many are less than 10 mm in size when diagnosed by screening. Additionally, after a course of neo-adjuvant chemotherapy, the tumour may have shrunk to only a few millimetres in size. The cancer may spread to the local lymph nodes and these may also benefit from implant hyperthermia treatment. Lymph nodes are typically less than 10 mm in size and many are less than 6 mm in size. In order to treat them effectively, the treatment needs to focus on the diseased area while minimising damage to surrounding healthy tissue. It is therefore desirable for a hyperthermia implant for treating a lymph node to be able to fit within the node.

Magnetic nanoparticle hyperthermia is known in the art (for example, see Dutz S and Hergt R. Magnetic nanoparticle heating and heat transfer on a microscale: basic principles, realities and physical limitations of hyperthermia for tumour therapy. Int J Hyperther 2013; 29:790-800). However, the concentration of iron oxide nanoparticles needed for effective thermotherapy is high and this limits the clinical applications in which magnetic nanoparticle hyperthermia is used.

Magnetic seed hyperthermia is also known in the art (for example, see EP0333381) where a magnetic field is used to induce Eddy current or magnetic hysteresis heating in a metallic seed. The seed preferably has an elongated aspect ratio partly in order to reduce the demagnetisation factor so as to increase the heating response, and also in order to facilitate introduction into the body through a needle. The drawback of these systems is that the elongated aspect ratio (e.g. length:diameter ratio being at least 10 and often 20 or more) means that in order to maximise the response, the seed orientation with respect to the magnetic field must be known. EP0333381 notes that when the orientation of the needle is not known precisely or the coils cannot be located properly, it may be necessary to provide a coil arrangement employing three coils each set at right angles to each other. The coils are energized one at a time in a repetition sequence by a standard time sharing power source. This means that dependent on the orientation of the seed, the seed may only be subjected to full field strength for one-third of each cycle of the power source. The orientation versus field needs to be controlled for optimum results. This arrangement adds significant complexity to the coils.

In a similar way, glass-coated microwires are known in the art for heating via magnetic losses due to the large Barkhausen jump (LBJ) in their magnetisation curve, (see for example, "High Performance Soft Magnetic Materials": Springer Series in Materials Science, Volume 252. ISBN 978-3-319-49705-1). Glass coated microwires produce only a small amount of heat because of their very small size (typically 10-50 μm in diameter) and thus many need to be used together to generate clinically useful heating. The heating is also orientation dependent relative to the magnetic field axis.

Iron- or cobalt-based microwires with a LBJ in their magnetisation curve are also known in the art for use as magnetic markers, although not for hyperthermia. See for example U.S. Pat. No. 4,66,025, EP0961301, EP0710923, JP2003 308576, U.S. Pat. No. 6,230,038, and EP1258538. A length to diameter ratio of at least 200 or more is required for effective generation of the switching or magnetisation reversal behaviour characteristic of such LBJ wires. In order to achieve this ratio with the typical wire diameters that are manufacturable (in the 30 μm to 125 μm range), the prior art further teaches that a wire with a length of more than 10 mm and more typically more than 25 mm is required. Thus none of these markers would be suitable for marking a small tumour or lymph node.

It is clear that a significant problem with prior art approaches is that the implant needs to be aligned with the magnetic field in order to maximise the heating effect. It is desirable to provide an implant for hyperthermia treatment that meets all the requirements of an implant including small size (<10 mm long); ability to be delivered through a small needle (eg. 16 g-18 g); and robust for implantation and surgical removal, while also able to provide a substantially uniform heating output regardless of the orientation of the implant relative to the direction of the magnetic field exciting the implant.

The Applicant's co-pending, published European Publication No. EP 3517068 A1 claiming priority from GB1801224.5, the contents of which are incorporated herein by reference, describes a detection system and method that uses an implantable magnetic marker comprising at least one piece of a large Barkhausen jump material (LBJ). The marker is deployed to mark a tissue site in the body for subsequent surgery, and the magnetic detection system includes a handheld probe to excite the marker below the switching field for bistable switching of the marker causing a harmonic response to be generated in a sub-bistable mode that allows the marker to be detected and localised. The marker implanted may be shorter than the critical length required to initiate bistable switching of the LBJ material.

It is an aim of the present invention provide an improved hyperthermia implant that overcomes, or at least alleviates, the above-mentioned drawbacks.

SUMMARY OF THE INVENTION

According to a first aspect of the present invention there is provided a hyperthermia implant comprising at least one piece of magnetic material that exhibits a large Barkhausen jump (LBJ) in its magnetisation curve wherein the implant is configured to provide a magnitude of heating that is substantially independent of the orientation of the implant with respect to the axis of an applied magnetic field (X).

Preferably, the implant comprises multiple portions of magnetic material arranged in different planes, the portions being configured such that there is always at least one of the portions of the magnetic material at most 60°, more preferably at most 55° from any axis through the implant.

Preferably, the implant is configured to provide at least a portion of the magnetic material that is always at most 60°, more preferably at most 55° from any axis through the implant thereby providing a portion that is at most 60°, more preferably at most 55° from the applied magnetic field axis (X).

According to a second aspect of the present invention there is provided a hyperthermia implant according to the first aspect of the invention for use in the hyperthermia treatment of tissue in a human or animal body.

Preferably, the implant comprises less than 2 mg and more preferably less than 1 mg of LBJ material in order that the amount of material implanted in the body is minimised. The material may be provided in the form of a wire. Examples of such materials include, but are not limited to, iron-, cobalt- and nickel-rich glass-coated amorphous microwires, iron-silicon-boron based amorphous microwires, iron- or cobalt-based amorphous microwires, and/or bulk metallic glass wires, but any material in which a LBJ response can be excited may be suitable. The wires may be coated and/or provided within a hollow tube and/or may be deployable from an initial compact configuration to an extended, deployed configuration. Preferably, the implant is deployable from a needle having an inner diameter of less than 2 mm in order to minimize the trauma and pain associated with implantation.

Preferably, the implant provides a substantially similar magnitude of heating effect regardless of its orientation with respect to the axis of the magnetic field that is exciting the implant. This is important in order to provide consistent heating without the need to orient the magnetic field and the marker in a particular position with respect to each other. If the heating effect does vary according to the relative orientations of the marker and the exciting magnetic field, the amount of heating may not be easily predictable and may be either insufficient in the case of an 'unfavourable' orientation where the magnetic coupling between the marker and the field is small, or too intense in the case where the coupling is strong. The marker orientation may not be known once the implant has been placed in the body, and from a surgical perspective it is undesirable to have to ensure or confirm that the marker is placed in a particular orientation. Once implanted, it is not usually possible to alter the position or orientation of the marker in the tissue except by moving the patient which may not be possible or desirable.

In a preferred embodiment, the implant is configured to provide a magnitude of heating that is substantially independent of the orientation of the implant with respect to the axis of the applied magnetic field.

In a preferred embodiment, the implant is provided in the form of a coiled microwire. In another embodiment, the implant may have a further length of microwire along the central axis of the coiled wire. In another preferred embodiment, the implant may comprise a three-edged or four-edged tetrahedron, for example, comprising three or four microwires arranged to form three or four edges respectively of a tetrahedron or the implant may comprise a three-legged tripod, for example, comprising three microwires arranged to form three legs of a tripod. These configurations have been shown to provide a magnitude of heating that is substantially independent of the orientation of the implant with respect to the magnetic field axis.

A third aspect of the present invention provides a hyperthermia system for heating a hyperthermia implant in a tissue of a body, the system comprising:

at least one hyperthermia implant, the implant comprising at least one piece of magnetic material that exhibits a large Barkhausen jump (LBJ) in its magnetisation curve;

at least one drive coil arranged to excite the implant with an alternating magnetic field; and a magnetic field generator arranged to drive an alternating magnetic field through the at least one drive coil;

wherein excitation of the implant provides hyperthermia treatment of the surrounding tissue and wherein the implant is configured to provide a magnitude of heating that is substantially independent of the orientation of the implant with respect to the magnetic field axis.

Preferably, the frequency of the drive field is between 30 kHz and 750 kHz and the field strength is between 1000 A/m and 20,000 A/m. The frequency and field are chosen in order to minimise unwanted collateral damage to surrounding healthy tissue. The heating in surrounding tissue is proportional to the product of field and frequency fH and so the two parameters are chosen to keep the product below the level at which peripheral nerve stimulation or other tissue damage is experienced. The exact values will depend on the type of tissue and the cross section of the tissue or body at that place.

Preferably, where the implant comprises straight lengths of wire, the length of each of the pieces of LBJ material within the implant is below the critical length for that material type in the form it is being used e.g. wire, and preferably the length of each piece of straight wire is less than 10 mm and more preferably less than 6 mm.

Preferably, where the implant comprises straight lengths of wire, the length to diameter ratio of each wire is less than 100 and more preferably the ratio is in the range 50 to 100.

A fourth aspect of the present invention provides use of a system according to the third aspect of the present invention for the hyperthermia treatment of tissue in a human or animal body.

The third and fourth aspects of the present invention may include a temperature sensor for providing feedback on the temperature of the implant. Preferably the temperature sensor communicates with a controller for adjusting the strength of the magnetic field applied by the drive coil.

A further aspect of the present invention provides a combined detection and hyperthermia treatment system for locating and heating an implant in a body, the combined system comprising:

at least one implantable marker, the implantable marker comprising at least one piece of magnetic material that exhibits a large Barkhausen jump (LBJ) in its magnetisation curve;

at least one drive coil arranged to excite the marker with an alternating magnetic field and at least one sense coil arranged to detect a signal received from the excited marker;

a magnetic field generator arranged to drive an alternating current through the at least one drive coil so as to generate an alternating magnetic field from the coil; and at least one detector arranged to receive the signal from the sense coil and detect one or more harmonics of the drive frequency in the received signal, wherein the at least one drive coil excites the marker below the switching field required to initiate bistable switching behaviour of the LBJ material of the marker;

the system further comprising at least one drive coil for excitation of the marker to provide heating of the surrounding tissue, the marker being configured to provide a magnitude of heating that is substantially independent of the orientation of the marker with respect to the magnetic field axis.

It is to be appreciated that the at least one drive coil that excites the marker for detection may be the same drive coil that excites the marker for hyperthermia treatment.

In one embodiment, the at least one drive coil excites the implant below the switching field required to initiate bistable switching behaviour of the LBJ material of the implant. Large Barkhausen Jump materials, also known as LBJ materials, bistable switching materials or materials with large discontinuous changes in their magnetisation curve, undergo a rapid reversal of their magnetic polarization ("bistable switching" behaviour) when excited by an external magnetic field whose field strength opposing the instantaneous polarization of the material exceeds a predetermined threshold value, the switching field $H_{SW}$. In the present invention, the implant utilises a "sub-bistable" mode of excitation for its LBJ material that causes a measurable harmonic response to be sensed even when the excitation field is below that of the 'switching field'.

LBJ materials also have a critical length below which the bistable switching behaviour is not seen. Typically, the critical length of LBJ wires is of the order of between 20 mm and 60 mm. The concepts of 'critical length' and 'switching field' for LBJ wires are known from for example Vazquez (A soft magnetic wire for sensor applications., J. Phys. D: Appl. Phys. 29 (1996) 939-949). In order to initiate the bistable switching behaviour in a wire with a Large Barkhausen Jump in its magnetization curve, the wire must be greater than the 'critical length' and the driving field must be greater than a switching field $H_{SW}$.

Where the implant of the present invention comprises straight lengths of material, these lengths are preferably provided below the critical length required for the rapid reversal, generally being <25 mm, more preferably <10 mm, especially <6 mm, and having a length to diameter ratio of less than 200, and more preferably less than 100, this being preferable in order to reduce the size of the implant for convenient implantation and marking of smaller lesions.

The system preferably comprises an output module for processing the received harmonic signal and providing at least one indicator to the user relating to a location of the marker relative to the sense coil, for example an indication of the proximity, distance, direction or orientation of the marker with respect to the sense coil.

More preferably, the system processes one or more aspects of the harmonic response of the marker, such as the magnitude of one or more odd harmonics (eg, $3^{rd}$ and $5^{th}$), even harmonics (eg. $2^{nd}$, $4^{th}$ and $6^{th}$) or a combination of both or the ratios of these harmonics to each other or the fundamental frequency. Appropriate filters may be provided to enhance the sensed signals.

The output module may include a visual display or sound generator.

In one embodiment of this aspect of the invention, both the drive and sense coils are provided in a handheld probe to simplify the setting up of the system for the user.

In another embodiment of this aspect of the invention, both the drive and sense coils are provided in a configurable arm which can be moved to position the coils near the treatment area of the patient. The arm is preferably attachable to a portable unit which may be transported to the patient to facilitate the treatment.

According to a yet a further aspect of the present invention there is provided a method of hyperthermia treatment comprising implanting a hyperthermia implant in tissue of a human or animal body, the implant comprising at least one piece of magnetic material that exhibits a large Barkhausen jump (LBJ) in its magnetisation curve; and exciting the implant with an alternating magnetic field to provide hyperthermia treatment to the surrounding tissue, the implant being configured to provide a magnitude of heating that is substantially independent of the orientation of the implant with respect to the magnetic field axis.

The method may further comprise detecting the location of the implant, the method comprising applying an alternating magnetic field to the implant to excite the marker, the field being of a magnitude below the switching field required to initiate bistable switching behaviour of the LBJ material of the marker; and detecting one or more harmonics of the drive frequency of a signal received from the excited implant caused by a change in magnetization of the implant below its switching field.

Preferably, the drive frequency for detection is above 1 kHz, preferably being in the range 1-100 kHz, especially 10-40 kHz. The drive frequency for heating is preferably 30-750 kHz, preferably >250 kHz.

The method preferably includes measuring an aspect of the harmonic response of the implant to provide an output relating to its location. For example, this may be the amplitude of one or more odd harmonics, even harmonics or a combination of both, the ratios of these harmonics to each other or to the fundamental frequency. Appropriate filtering and processing of the signals may be provided to enhance the output provided by the method.

BRIEF DESCRIPTION OF THE DRAWINGS

For a better understanding of the present invention and to show more clearly how it may be carried into effect, reference will now be made by way of example only, to the accompanying drawings, in which:

FIG. 3 is a schematic diagram illustrating use of a magnetic seed hyperthermia treatment system according to the invention for treating breast cancer;

FIG. 4 is a schematic diagram illustrating an experimental set-up for investigating heating of a hyperthermia implant according to an embodiment of the present invention, shown with the hyperthermia implant positioned parallel to the magnetic field axis X;

FIGS. 8A and 8B illustrate two types of coiled hyperthermia implant according to embodiments of the present invention;

FIGS. 11A, 11B, and 11C illustrate three types of deployable implant, the implant of FIG. 11B being used for the heating effect shown in FIG. 10 and the implant of FIG. 11C being used for the heating effect shown in FIG. 17;

FIGS. 14A and 14B are respectively a schematic diagram and a block diagram of an embodiment of a detection system that may be combined with a hyperthermia treatment system according to the present invention;

FIG. 16 illustrates a further deployable implant according to the present invention showing the angles between the long axis of each microwire in the implant and the axis of the magnetic field applied to heat the implant; and FIG. 17 is a graph illustrating heating effect in four orientations of a magnetic seed hyperthermia implant according to another embodiment of the present invention, the implant having a four-edged tetrahedron comprising four amorphous microwires of length 4.8 mm.

DETAILED DESCRIPTION OF THE INVENTION

The present invention relates to a hyperthermia implant that can be implanted into tissue requiring hyperthermia treatment. The implant comprises at least one piece of magnetic material that exhibits a large Barkhausen jump (LBJ) in its magnetisation curve. The invention also provides a hyperthermia system for heating the hyperthermia implant in a tissue of a body, the system comprising at least one hyperthermia implant, the implant comprising at least one piece of magnetic material that exhibits a large Barkhausen jump (LBJ) in its magnetisation curve; at least one drive coil arranged to excite the implant with an alternating magnetic field; and a magnetic field generator arranged to drive an alternating magnetic field through the at least one drive coil; wherein excitation of the implant provides hyperthermia treatment of the surrounding tissue. The hyperthermia system may be housed in a static unit or in a portable unit for convenient access to the patient.

For clarity, "a magnetic material that exhibits a large Barkhausen jump (LBJ) in its magnetisation curve" refers to a material which, if provided in a suitable geometry and size or length, and driven by suitable magnitude and frequency of magnetic field, can generate a rapid reversal in its magnetisation known as a Large Barkhausen Jump. Any particular wire used in one of the examples or embodiments may not be sufficiently sized or shaped and may not be driven by an appropriate field to create the rapid reversal in its magnetisation, but the 'LBJ' description refers to its magnetic material properties such that a piece of material with the same magnetic material properties if of the right geometry and size and driven by the appropriate field could generate the rapid reversal in magnetisation.

It has been found that the magnetic hyperthermia implant according to the present invention provides a substantially uniform heating output regardless of the orientation of the implant relative to the direction of magnetic field exciting the implant, thus ensuring effective heating of the implant during treatment. Furthermore, the implant may be provided in a small size (<10 mm long) prior to deployment, may be delivered through a small needle (16-18 g) and is robust for implantation and surgical removal.

Figure 1:
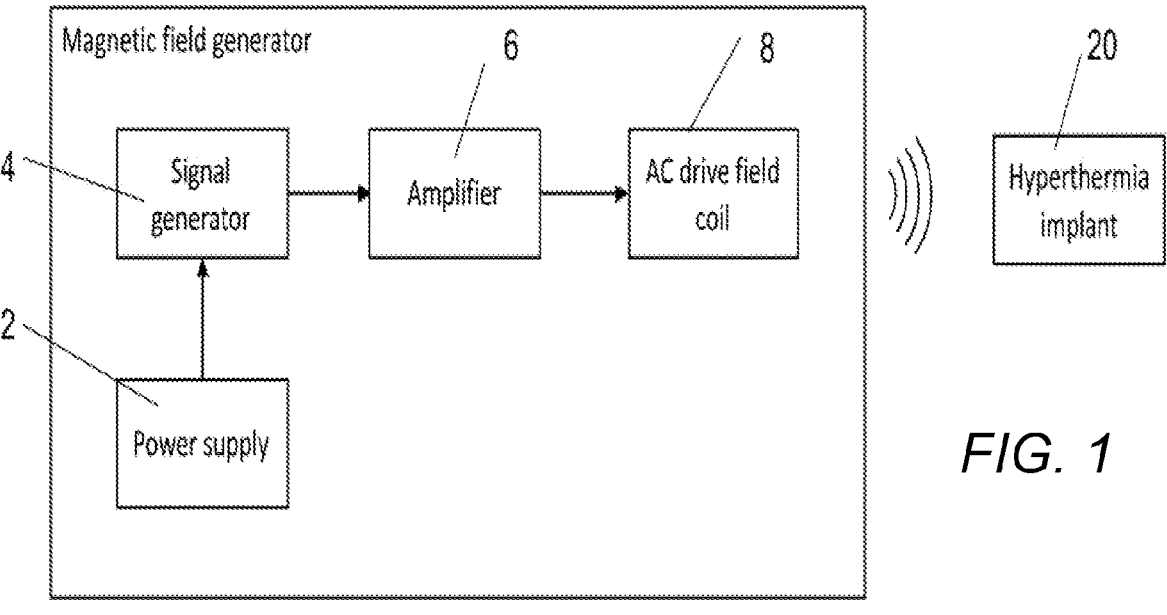
FIG. 1 is a block diagram of a magnetic seed hyperthermia treatment system according to one embodiment of the present invention.
Figure 2:
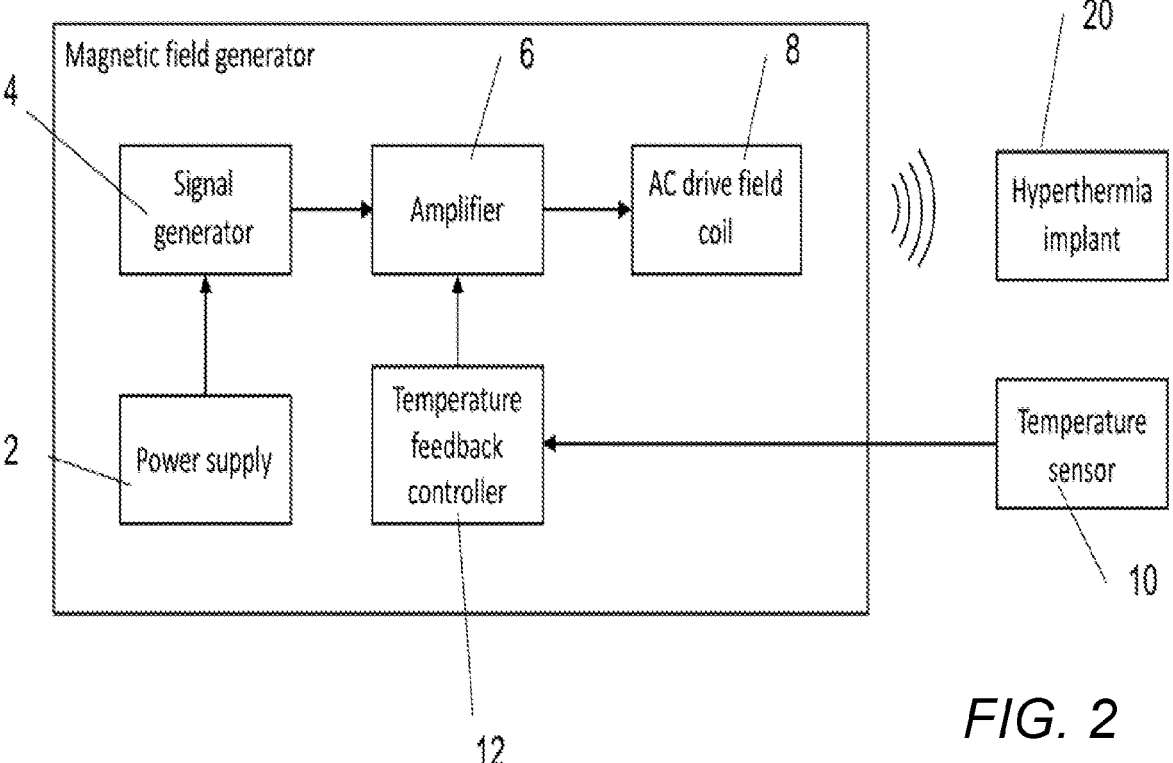
FIG. 2 is a block diagram of a magnetic seed hyperthermia treatment system according to another embodiment of the present invention.

FIGS. 1 and 2 of the accompanying drawings illustrate the basic components of a hyperthermia treatment system according to two embodiments of the present invention. A hyperthermia implant 20 according to the invention is inserted into an area of tissue requiring treatment. A power supply 2 connected to a signal generator 4, amplifier 6 and AC drive field coil 8 is then able to excite the implant 20 causing the heating thereof. Optionally, a temperature sensor 10 may be provided to monitor the temperature of the implant with a temperature feedback controller 12 feeding back this data to the amplifier 6 to control the temperature output of the implant, as shown in FIG. 2.

FIG. 3 illustrates a hyperthermia treatment system according to the invention for use in the treatment of breast cancer. An implant 20 according to the invention is placed in a tissue area requiring heat therapy, such as in a tumour 30 located in breast tissue. A base unit 1 includes the signal generator and amplifier for supplying an alternating current or voltage to a handpiece 14 which includes the drive coil, the current or voltage from the base unit driving a magnetic field in the coil in the handpiece. The handpiece is placed in the vicinity of the tissue to be treated and the coil in the handpiece creates an alternating magnetic field which serves to magnetize the hyperthermia implant 20. The alternating magnetisation in the implant generates heat in the implant through magnetic hysteresis losses or Eddy currents, which either destroys the cells directly, or activates various cellular processes in the tumour cells so that they undergo apoptosis or enhances the ability of the immune system to recognise and kill the tumor cells. The drive coil may further be mounted on an arm connected to a portable unit that sits on the ground or on a convenient surface, to facilitate treatment without the need to hold the unit with a hand.

Most breast cancers when diagnosed are smaller than 20 mm in diameter and many are smaller than 10 mm in diameter particularly if they are diagnosed by screening programmes. Additionally, lymph nodes requiring treatment are typically less than 8 mm in size and often 4 to 6 mm in size. When treating the cancer it is important to treat the diseased tissue but to minimise damage to healthy tissue surrounding the tumour. Thus the size of the hyperthermia implant is an important factor, and for these early stage cancers, a small implant is preferred with an overall diameter once deployed of less than 20 mm and more preferably less than 10 mm (i.e. the marker would substantially fit within a sphere of this diameter). This implies that where straight pieces of wire are used, the lengths of these wires needs to be less than 10 mm in length. However, for conventional wires exhibiting a LBJ in their magnetisation curve, this presents a problem because 10 mm is below the critical length of the wire and thus the switching behaviour would not be seen. This is explained in a number of prior art patents for magnetic markers using wires with a LBJ whose teaching clearly encourages increased length of wire and a high ratio of wire length to wire diameter in order to see the switching behaviour. See for example U.S. Pat. No. 4,660, 25, EP0961301, EP0710923, JP2003 308576, U.S. Pat. No. 6,230,038, and EP1258538. None of these disclose a wire with a length of less than 10 mm and none disclose a length to diameter ratio of less than 200, with the typical values disclosed being in the range 200 to 400. In this respect, a high length to diameter ratio is considered necessary for effective generation of the switching or magnetisation reversal behaviour. Furthermore, given the typical range of diameters of the microwires used for these markers (in the region of 30 μm to 125 μm) maximising the length of the wire is the primary way to achieve the required high length to diameter ratio. Hence this prior art teaches that a microwire of less than 10 mm in length with a length to diameter ratio of less than 200 would not provide the desired switching behaviour.

Surprisingly, the inventors have found that a piece of such wire less than 10 mm in length and with a length to diameter ratio of less than 200 is able to produce effective heating when excited using a sub-bistable mode of excitation. Length to diameter ratio is defined as the length of a straight wire divided by the largest cross-sectional diameter of the wire. Where the wire does not have a circular cross section, for example in the case of a rectangular section, the diameter is taken to be the longest diagonal dimension of the cross section.

Where straight pieces of the LBJ magnetic material are used, these pieces of wire in the marker may also be provided below the critical length of the LBJ material required to enable bistable switching behaviour, e.g. below 10 mm and with a length to diameter ratio of less than 200.

The 'critical length' of an embodiment of an LBJ implant of the present invention (such as "e" in Example 1 below) is around 40 mm, meaning that wires of this material which are shorter than 40 mm cannot exhibit the Large Barkhausen Jump switching behaviour. Thus it will be appreciated, that while the implant of the present invention requires a material with a LBJ in its magnetisation curve because such materials give improved heating, the implant used (where a straight length of wire is used) is below the critical length and therefore too short for the LBJ switching behaviour to be seen. The prior art would suggest that LBJ wires are not useful when used in lengths below their critical length, but the inventors have surprisingly found that while the heating effect of the present invention requires LBJ wire materials and the magnetic properties they possess, it does not rely on the LBJ switching behaviour described in the prior art for its function.

Table 1 below shows the results from testing the heating effects of various types of seed implant, according to the present invention, using the apparatus shown in FIG. 4 with an applied magnetic field of 5 kA/m at a frequency of 525 kHz. The LBJ magnetic microwires have various different compositions, diameters and lengths. In each case, a measurable heating effect can be seen. The wires range in length from 2 mm to 8.4 mm, and thus all are suitable for use in a hyperthermia implant. The length to diameter ratio of the wires ranges from 14 to 87. While wires with a higher length to diameter ratio tend to give improved heating, even some with a very low ratio of length to diameter give adequate performance, for example rows 2 and 10 in Table 1 where the length to diameter ratios are 33.6 and 28 respectively. The conventional manufacturing process for such amorphous microwires usually results in a wire of diameter between 30 nm and 125 nm, and more usually around 100 nm in diameter. Thus if the wire needs to be less than 10 mm in length, the ratio of length to diameter will necessarily be less than 100. Thus an optimal range of length to diameter ratio is high enough to achieve adequate heating i.e. greater than 15, but low enough so that the wire is not too long for use in an implant i.e. less than 200 for wires of diameter 50 nm or less, and more preferably the ratio is less than 100 where the wire diameter is around 100 nm and more preferably in the range 50 to 100.

TABLE 1

| Material | Microwire diameter (mm) | Microwire length (mm) | Length: Diameter ratio | Temperature rise when heated with 5kA/m @ 525 kHz (° C.) |
|---|---|---|---|---|
| 1. Iron-based | 0.125 | 2 | 16 | 6.7 |
| 2. Iron-based | 0.125 | 4.2 | 33.6 | 25.2 |
| 3. Iron-based | 0.125 | 8.1 | 87 | 52.9 |
| 4. Cobalt-based | 0.1 | 2 | 20 | 3.9 |
| 5. Cobalt-based | 0.1 | 4 | 40 | 18.4 |
| 6. Cobalt-based | 0.1 | 5.1 | 51 | 28.5 |
| 7. Cobalt-based | 0.1 | 6 | 60 | 34.2 |
| 8. Cobalt-based | 0.1 | 8 | 80 | 42 |
| 9. Cobalt-based | 0.3 × 0.04 rectangular section | 4.2 | 14 | 7.5 |
| 10. Cobalt-based | 0.3 × 0.04 rectangular section | 8.4 | 28 | 23.2 |

Various other experiments were carried out to investigate the heating effect of a hyperthermia implant according to the present invention and to compare this with other prior art hyperthermia implants.

EXAMPLE 1

Investigation into the Heating Effects of a Hyperthermia Implant According to an Embodiment of the Invention and Various Other Types of Hyperthermia Seed Implants.

Magnetic hyperthermia experiments were carried out to investigate the heating effects of various types of seed implant, including the implant of the present invention, using the apparatus shown in FIG. 4.

Five different types of material for the implant were investigated, as detailed below:
(a) Ferritic stainless steel, diameter 0.9 mm×length 5 mm;
(b) Copper wire, diameter 0.1 mm×length 5.7 mm;
(c) Amorphous high permeability microwire without LBJ, diameter 0.1 mm×length 5.5 mm;
(d) Manganese Iron ferrite, diameter 1.0 mm×length 5.3 mm;
(e) Amorphous microwire with LBJ, diameter 0.1 mm×length 5.9 mm.

Each implant 20 was placed in a vial 42 containing 0.25 ml of water 40, the vial being surrounded by a water-cooled hyperthermia coil 8 for activating the implant and the temperature rise of the water is recorded. Each implant (a) to (e) was tested in two orientations; parallel to the magnetic field axis X (as shown in FIG. 4) and perpendicular to the magnetic field axis. The implants are excited by a field of 5000 A/m at a frequency of 525 kHz.

Figure 5:
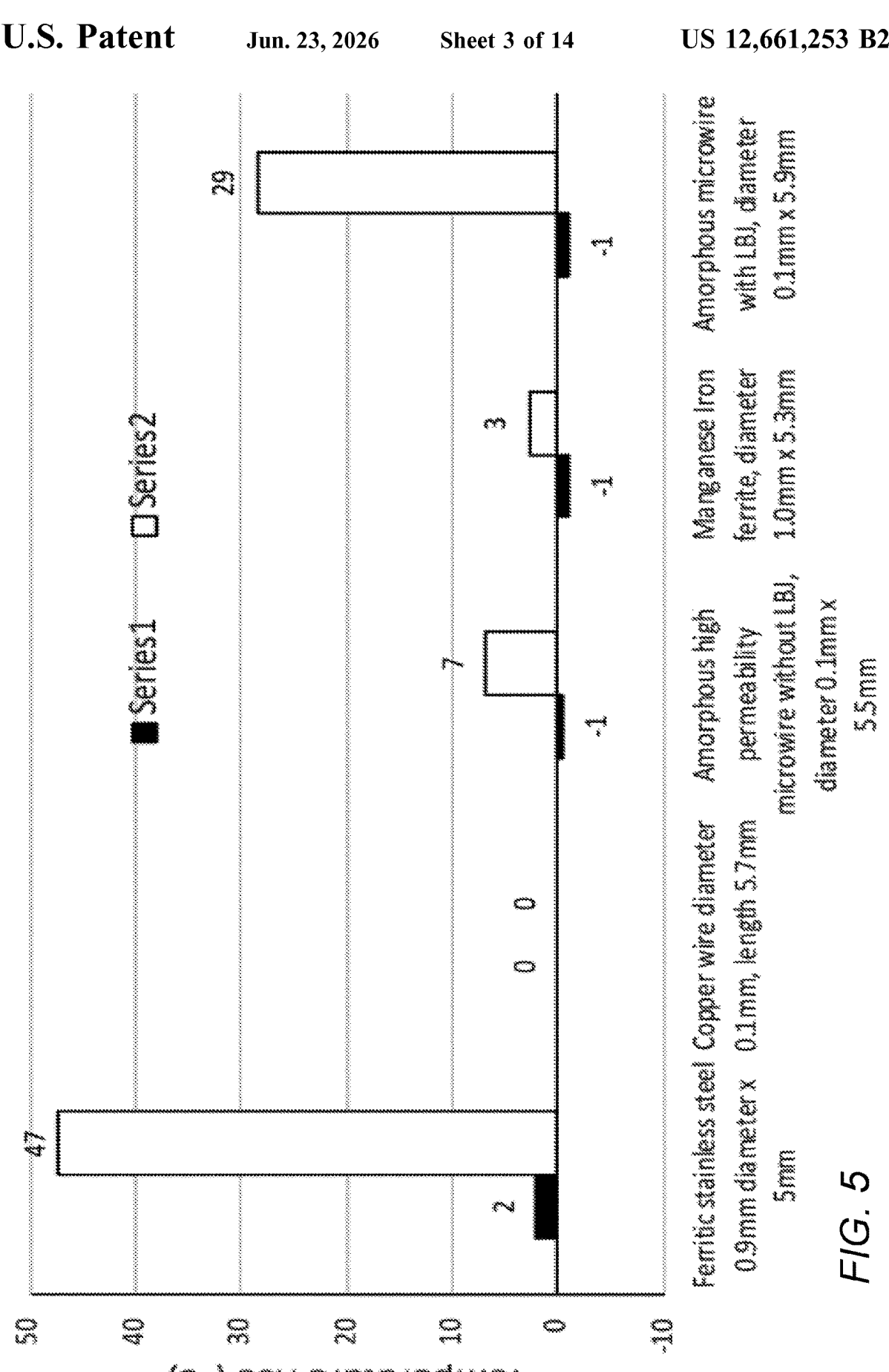
FIG. 5 is a graph illustrating heating effect for various types of seed implant using the experimental set-up shown in FIG. 4.

The results are illustrated in FIG. 5, with Series 1 showing the results for when the implant is perpendicular to the magnetic field and Series 2 showing the results for when the implant is parallel to the magnetic field. The results show that implant (a) made from ferritic stainless steel generates a significant heating response when parallel to the field but minimal response when perpendicular to the field. The ferrite also produces a higher response parallel to the field but the magnitude of the response is much reduced.

Three wires of similar dimensions (b), (c) and (e) were also tested. A copper wire which is non-magnetic produced no heating effect in either direction. An amorphous microwire with high permeability but no LBJ in its magnetisation curve produced a moderate response when parallel to the field but none perpendicular to the field. This suggests that the heating in the magnetic wires is enhanced by the magnetic properties of the material, either directly due to magnetic hysteresis in the magnetisation curve, or because the magnetic material concentrates the magnetic field in the implant causing increased Eddy current losses in the wire. In contrast, there is no heating in the copper wire which is non-magnetic but highly conductive. The amorphous microwire with high permeability and a LBJ in its magnetisation curve (e) produced a strong heating response when parallel to the field and none perpendicular to the field. This shows that the presence of the LBJ in the wire is important for improved heat generation.

Figure 6:
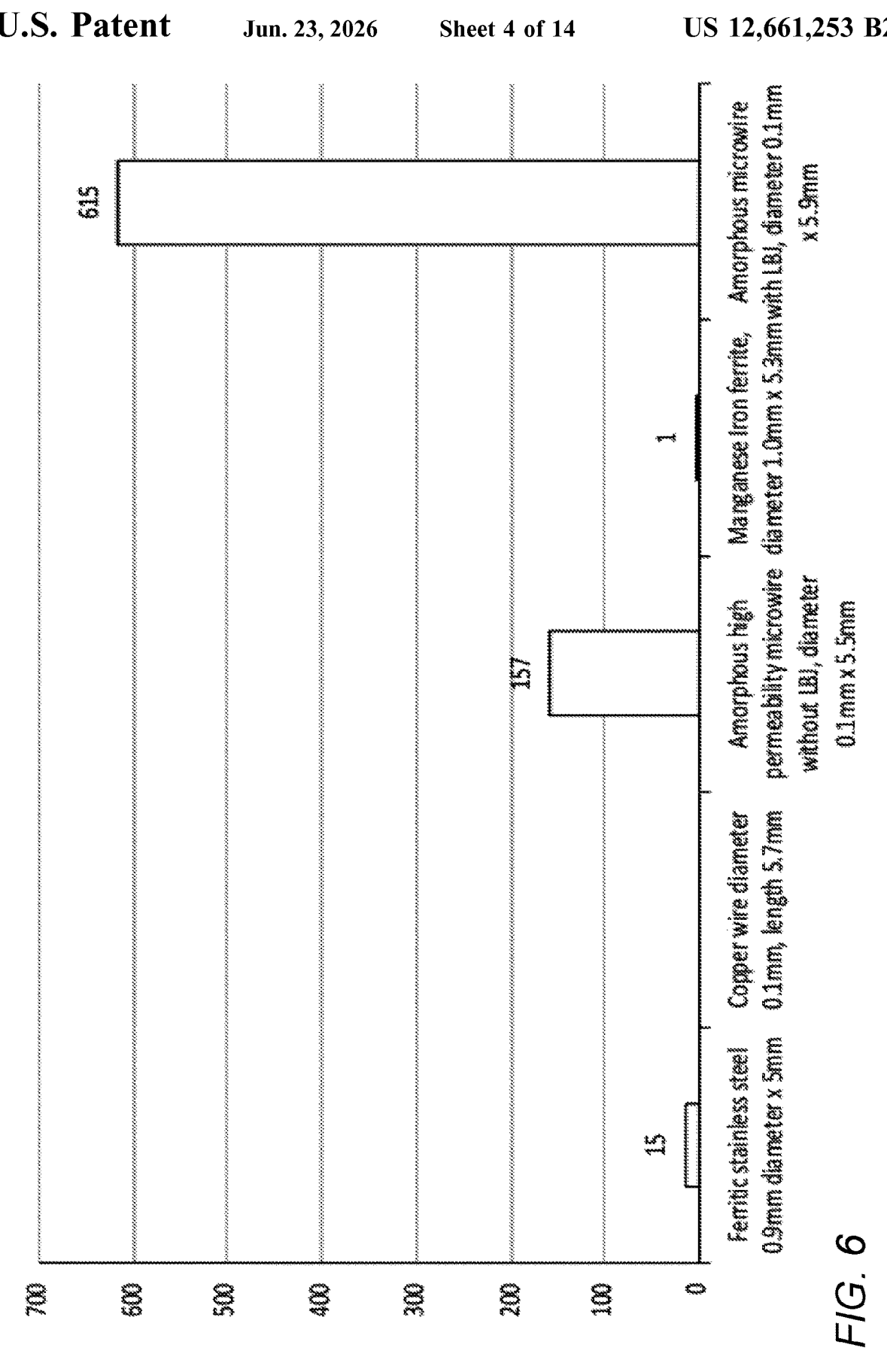
FIG. 6 is a graph illustrating heating effect for various types of seed implant normalised by seed volume.

The data obtained in FIG. 5 was normalised by the volume of the implants (i.e. the temperature increase was divided by the volume of the implant) to show the heating effect per unit volume of implant. The results are shown in FIG. 6. This shows that compared to a ferritic stainless steel (a), the high permeability implant (c) improves the heating by a factor of 10, whereas the LBJ implant of the present invention (e) improves the heating by a factor of 40 times, further demonstrating the importance of the LBJ in the magnetisation curve for increasing the heating effect provided by the implant. The increased heating effect may be due to increased hysteresis losses in the wire or because the magnetisation of the wire concentrates the magnetic field more strongly in the wire or via another mechanism.

EXAMPLE 2

Investigation into the Effects of the Orientation Relative to the Magnetic Field Axis of a Hyperthermia Implant According to an Embodiment of the Invention on the Heating Effect of the Implant.

The effect of the orientation relative to the magnetic field axis of the hyperthermia implant according to the invention was investigated using the experimental set up shown in FIG. 4.

Figure 7:
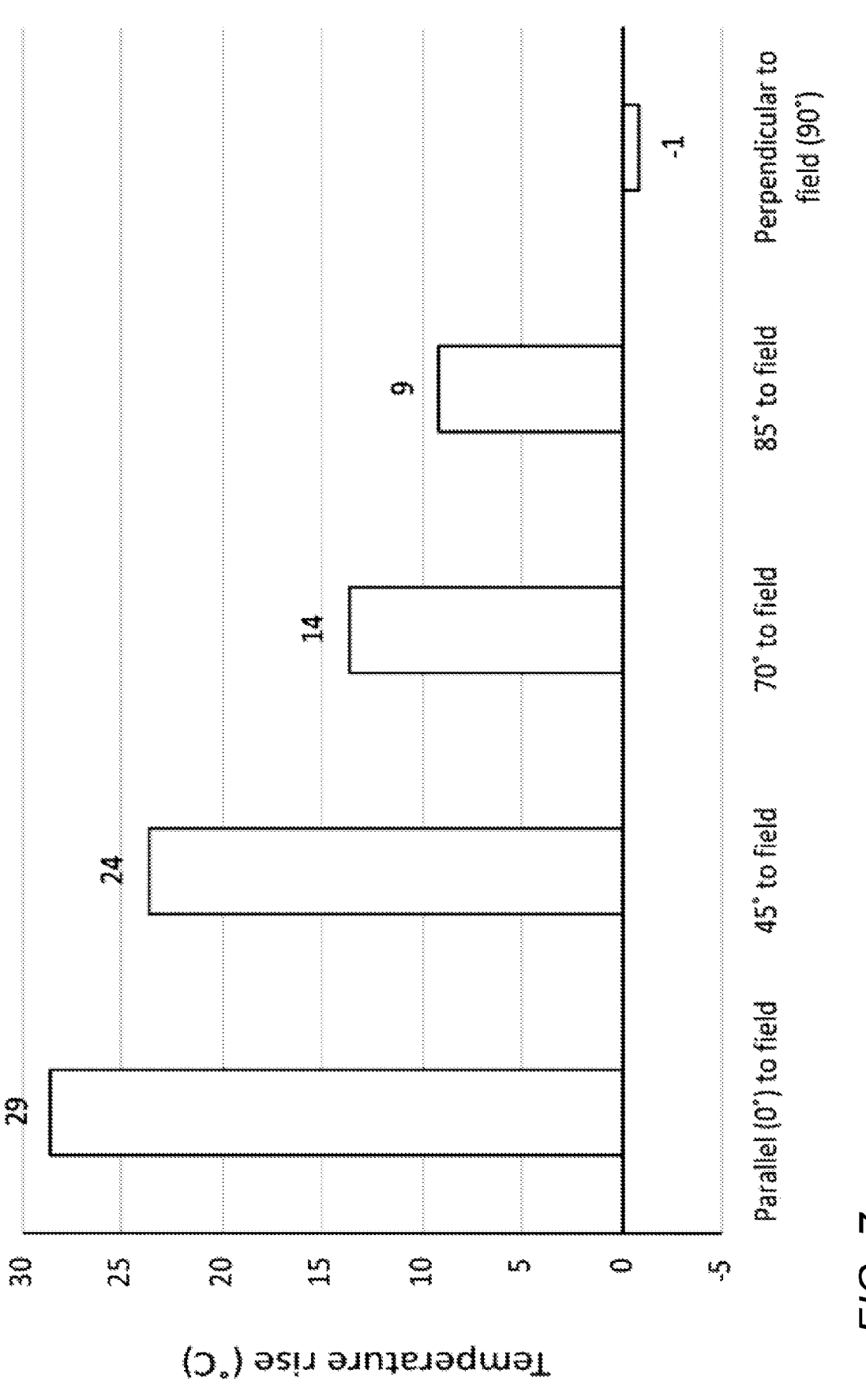
FIG. 7 is a graph illustrating heating effect of various orientations relative to the magnetic field axis X of a magnetic seed hyperthermia implant according to an embodiment of the present invention.

FIG. 7 shows the heating effect from the amorphous microwire with LBJ (e) at various orientations with respect to the magnetic field axis X. The maximum effect is obtained parallel to the field and significant heating is also achieved when the implant is at 45° to the field, thus illustrating that there may be some variation in the orientation of the implant with respect to the magnetic field axis. At 70° to the field the heating is reduced to around half the maximum. Thus, to maximise the heating effect it is desirable to have the implant within 70° and more preferably within 45° of the field axis. However, practically this may be difficult to achieve as it requires knowledge of the orientation of the implant and access from the required angle for the field.

EXAMPLE 3

Investigation into the Effects of the Orientation Relative to the Magnetic Field Axis of a Hyperthermia Implant According to Two Embodiments of the Invention on the Heating Effect of the Implant.

Two different configurations of amorphous microwire with LBJ were investigated to assess their suitability for use as a hyperthermia implant according to the invention. One implant comprises a coiled microwire with LBJ as shown in FIG. 8A and the other comprises a coiled LBJ microwire provided with a further piece of amorphous LBJ wire running through the axial core, as shown in FIG. 8B.

Figure 9:
FIG. 9 is a graph illustrating heating effect of the implants of FIGS. 8A and 8B, the implants having a coiled microwire with and without an axial core, in two orientations relative to the magnetic field axis X.

FIG. 9 shows the heating effect obtained from implants illustrated in FIGS. 8A and 8B, in two orientations (perpendicular and parallel to the magnetic field).

A coil comprising the microwire in a fine stainless steel tube which is then formed into a coil (FIG. 8A) surprisingly generates a significant heating effect when the coil axis is perpendicular to the field axis and minimal heating when the coil is aligned with the magnetic field axis. This is surprising because the LBJ wires are never usually used in a coil configuration because the LBJ effect is seen when the wires are straight and aligned with the field, and also because intuitively, the coil would be expected to produce a stronger heating effect when its long axis is aligned with the field.

When a further axial piece of the amorphous LBJ wire within a similar stainless steel fine tube is added to the coil running along its axis (FIG. 8B), the implant then generates a significant heating effect both when parallel and perpendicular to the field axis. Thus the coil implant with an axial core piece generates a substantially similar heating effect regardless of the orientation of the implant with respect to the magnetic field. Accordingly, this configuration of implant is particularly suitable for use as the hyperthermia implant.

The heating effect of the coil alone when aligned with the magnetic field is small but not zero. This small effect is because with a tightly wound coil, the wire forming the coil is primarily at right angles to the coil axis. This heating effect can be increased by increasing the pitch of the coil such that a larger portion of the coiled wire is within a 45° angle of the field axis. Thus at an optimal pitch, a single coil can produce a heating effect that is substantially independent of the orientation of the implant with respect to the magnetic field.

The coil may be in its final configuration before and after deployment. Alternatively, the coil may change configuration on deployment allowing a larger coil to be deployed from a fine gauge needle. In a preferred embodiment, the coil is uncoiled and substantially straight within the needle, but forms the coil shape on deployment. In a further embodiment, the coil is radially or axially compressed within the needle and expands on deployment to form a larger sized marker.

The coil preferably comprises between 1 and 20 turns and more preferably between 3 and 10 turns. Sufficient turns must be provided to provide enough magnetic material within the implant to generate a heating response. However, a higher number of turns makes the implant larger and more complex and expensive to manufacture.

EXAMPLE 4

Investigation into the Effects of the Orientation Relative to the Magnetic field Axis of a Hyperthermia Implant According to Another Embodiment of the Invention on the Heating Effect of the Implant.

The heating effect for a LBJ hyperthermia implant with a three-sided tetrahedron was investigated using the experimental set up shown in FIG. 4. The implant comprises three amorphous microwires of length 6 mm, as schematically shown in FIG. 11B of the accompanying drawings. The wires 60 are arranged to form three edges of a tetrahedron. In this case, to facilitate construction, the wires are enclosed in a PET sleeving 80 of thickness 0.33 mm.

Figure 10:
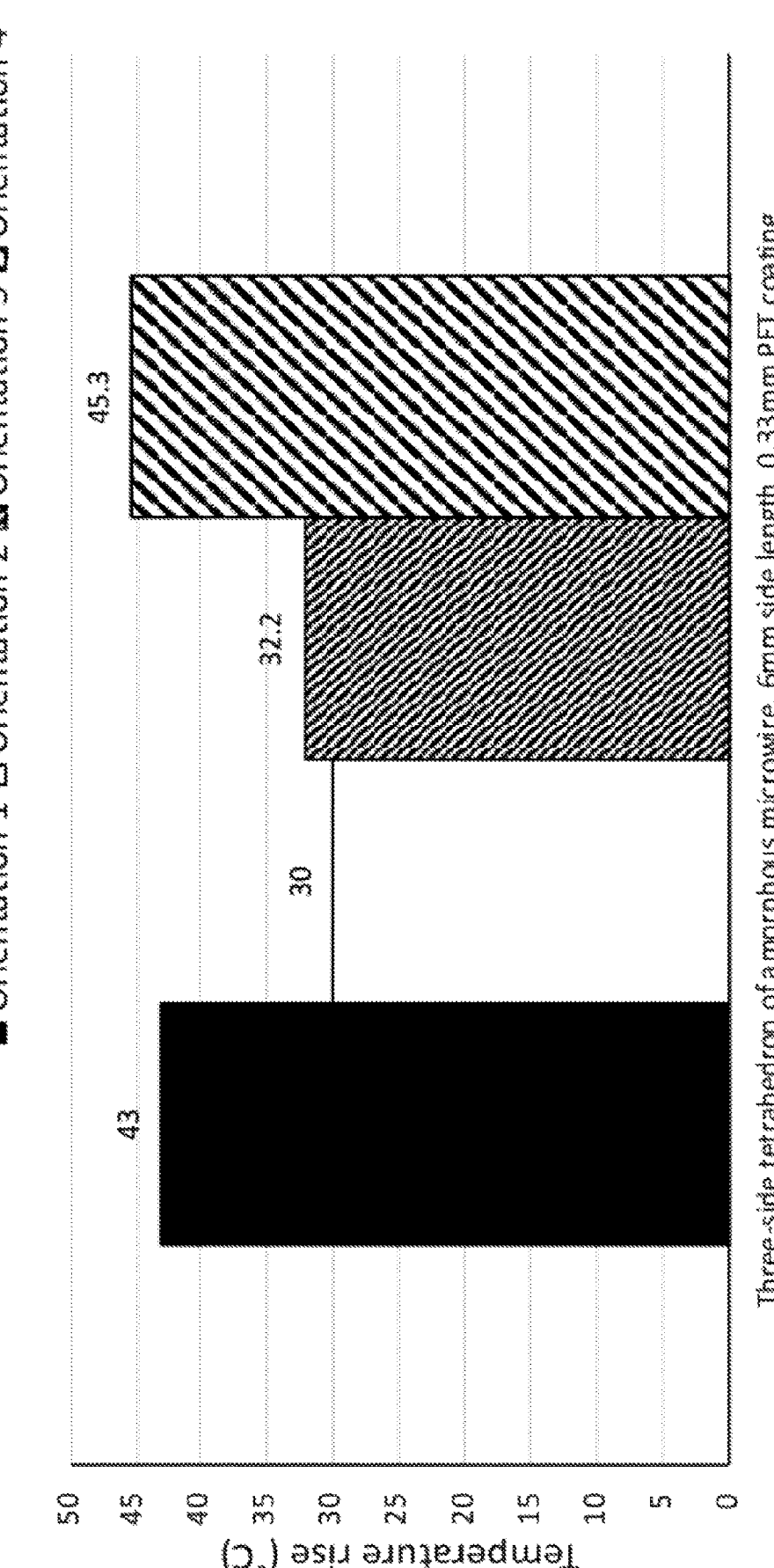
FIG. 10 is a graph illustrating heating effect in four orientations of a magnetic seed hyperthermia implant according to another embodiment of the present invention, the implant having a three-edged tetrahedron comprising three amorphous microwires of length 6 mm.

The graph of FIG. 10 shows the heating effect in four different orientations. There is significant heating in each orientation showing that the heating effect is substantially independent of the orientation of the implant with respect to the field axis. Accordingly, this configuration of LBJ implant is also highly suitable for use as a hyperthermia implant.

EXAMPLE 5

Investigation into the Effects of the Orientation Relative to the Magnetic Field Axis of a Hyperthermia Implant According to yet Another Embodiment of the Invention on the Heating Effect of the Implant.

The heating effect for a LBJ hyperthermia implant with a four-sided tetrahedron was investigated using the experimental set up shown in FIG. 4, although in this example the implant is heated within a vial containing 1.25 ml of water to accommodate the marker. The implant comprises four amorphous microwires 60' of length 4.8 mm, as schematically shown in FIG. 11C of the accompanying drawings. The wires are arranged to form four edges of a tetrahedron. In this case, to facilitate construction, the wires are enclosed in a nitinol sleeving 80' of outer diameter 0.26 mm and wall thickness of 50 nm.

The graph of FIG. 17 shows the heating effect in four different orientations. There is significant heating in each orientation showing that the heating effect is substantially independent of the orientation of the implant with respect to the field axis. Accordingly, this configuration of LBJ implant is also highly suitable for use as a hyperthermia implant.

It can be seen from the results of Examples 3, 4 and 5 that a heating effect that is substantially independent of the orientation of the implant with respect to the field axis (a 'uniform' heating effect) can be achieved in more than one way. Example 3 shows that a uniform heating effect can be achieved by a coil of microwire together with an axial wire. A similar effect can also be produced by a coil alone with a larger pitch angle. Examples 4 and 5 show that a uniform heating effect can be achieved through an implant comprising a number of pieces of microwire that are configured so that for any orientation of the applied magnetic field, there is a microwire partially aligned with the field. As Example 2 shows, the heating effect from a single wire increases as the angle between the wire axis and the axis of the applied magnetic field gets closer to zero, i.e. the wire needs to be at least partially aligned with the field for a heating effect to be seen. When the angle is 45°, the heating effect is about 85% of maximum, and when the angle is 70°, the heating effect is about half of the maximum. By interpolation of the values in FIG. 7, when the angle is 55°, the heating effect will be 70% of maximum and when the angle is 60°, the heating effect will be 62% of maximum.

FIG. 16 of the accompanying drawings illustrates a hypothetical marker according to the present invention comprising a number of straight microwires 60a, 60b, 60c in a magnetic field with axis X. Three of the microwires are shown. In FIG. 16, the wires are joined at one end, but in the general case it is not necessary to join the wires in this way and they could be separate, or joined in other configurations. The angle between each of n microwires and the field axis X is given by the angles $\varnothing_1, \varnothing_2, \varnothing_3 \ldots \varnothing_n$. Each angle is measured in the plane that includes both that wire axis and the axis of the field. For a marker comprising three or more straight microwires, preferably the value of the angle $\varnothing_n$ for at least one of the microwires is less than or equal to 55° for any orientation of the applied magnetic field axis X in order to ensure heating that is substantially independent of the orientation of the marker with respect to the field. In other words, the field axis is preferably never more than 55° from the axis of at least one microwire. For any configuration of wires, a maximum angle can be calculated that is the greatest angle that the field axis can be from aligning with a wire. In the case where there are three orthogonal microwires, the maximum angle is close to 55° . For the 3 edged tetrahedron marker of FIG. 11A (Example 4), the maximum angle is greater than 60°. For the four edged tetrahedron marker of FIG. 11C (Example 5) the maximum angle is between 40 and 60°.

The selection of an implant configuration in which the magnetic field axis X can never be more than 55° from at least one microwire, means that at least one microwire will be contributing at least around 70% of its maximum heating effect. Thus, by spacing the wires appropriately from each other, the heating effect can be made to be substantially independent of the orientation of the implant relative to the magnetic field axis X. It will be clear to one skilled in the art that this teaching can be applied to other geometries containing a number of straight wires: a preferred configuration is one chosen such that any axis in space passing through the implant (representing the axis of an applied field) is no more than 55° from the axis of one or more microwires. This configuration will have improved uniformity of heating with respect to orientation of the implant relative to the applied magnetic field. It will be appreciated that this condition is more easily achieved by having a larger number of microwires in the implant, but in order to make the implant simple to manufacture and deploy in the body through a small needle, the optimal number of straight microwires in an implant is between 3 and 6.

EXAMPLE 6

Investigation into the Heating Effects of Hyperthermia Implants According to Embodiments of the Invention and other Types of Implant Over Time.

Figure 12:
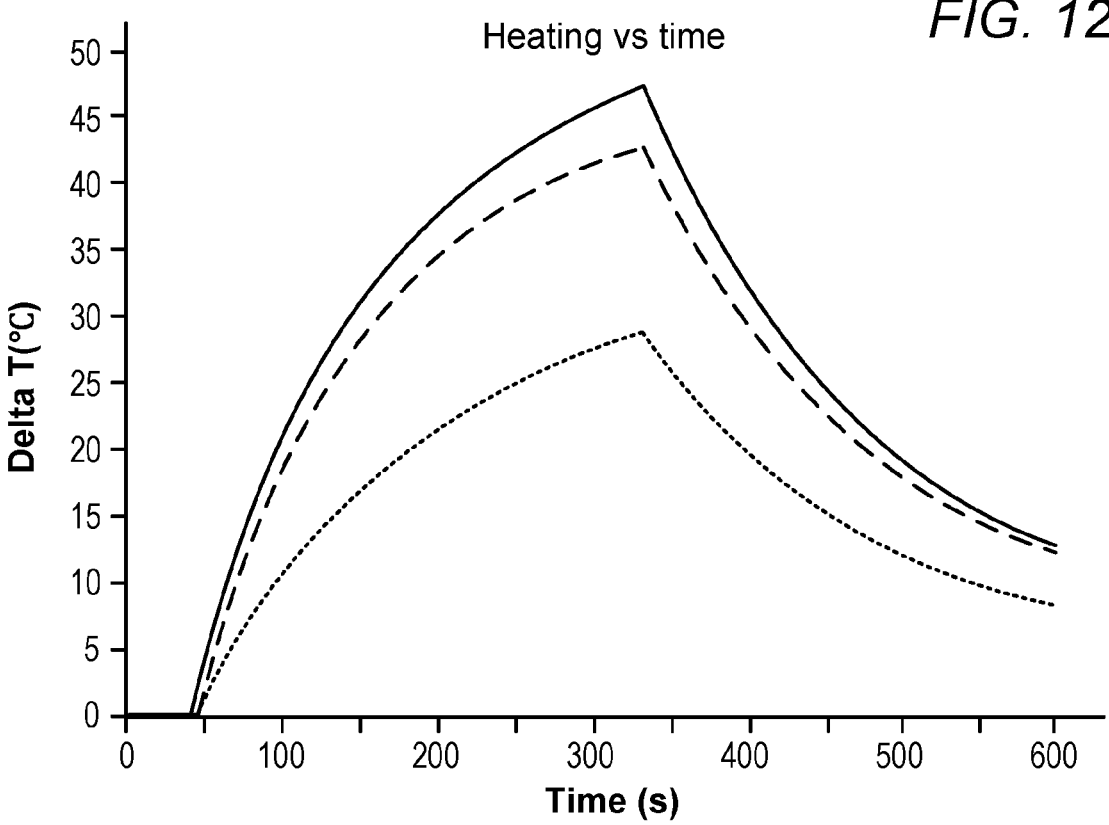
FIG. 12 is a graph showing heating versus time for various types of hyperthermia implants.

FIG. 12 is a graph showing heating versus time for various magnetic hyperthermia implants, in particular a ferritic stainless steel marker ('a' in Example 1), an amorphous high permeability microwire without LBJ ('c' in Example 1) and a three-sided tetrahedron of amorphous LBJ microwire with a PET coating (as used in Example 4 and shown in FIG. 11B). The heating effect is continuing to increase over a period of around 5 minutes before the field is switched off.

Thus, the present invention provides new hyperthermia implants that are of a size suitable for implantation and may be heated from multiple, orientations with respect to the axis of magnetic field, greatly enhancing the efficiency of the device.

EXAMPLE 7

Investigation into the Teating Effects of Hyperthermia Implants According to Embodiments of the Invention and Other Types of Implant with Different Field Strengths and Frequencies.

Figure 13:
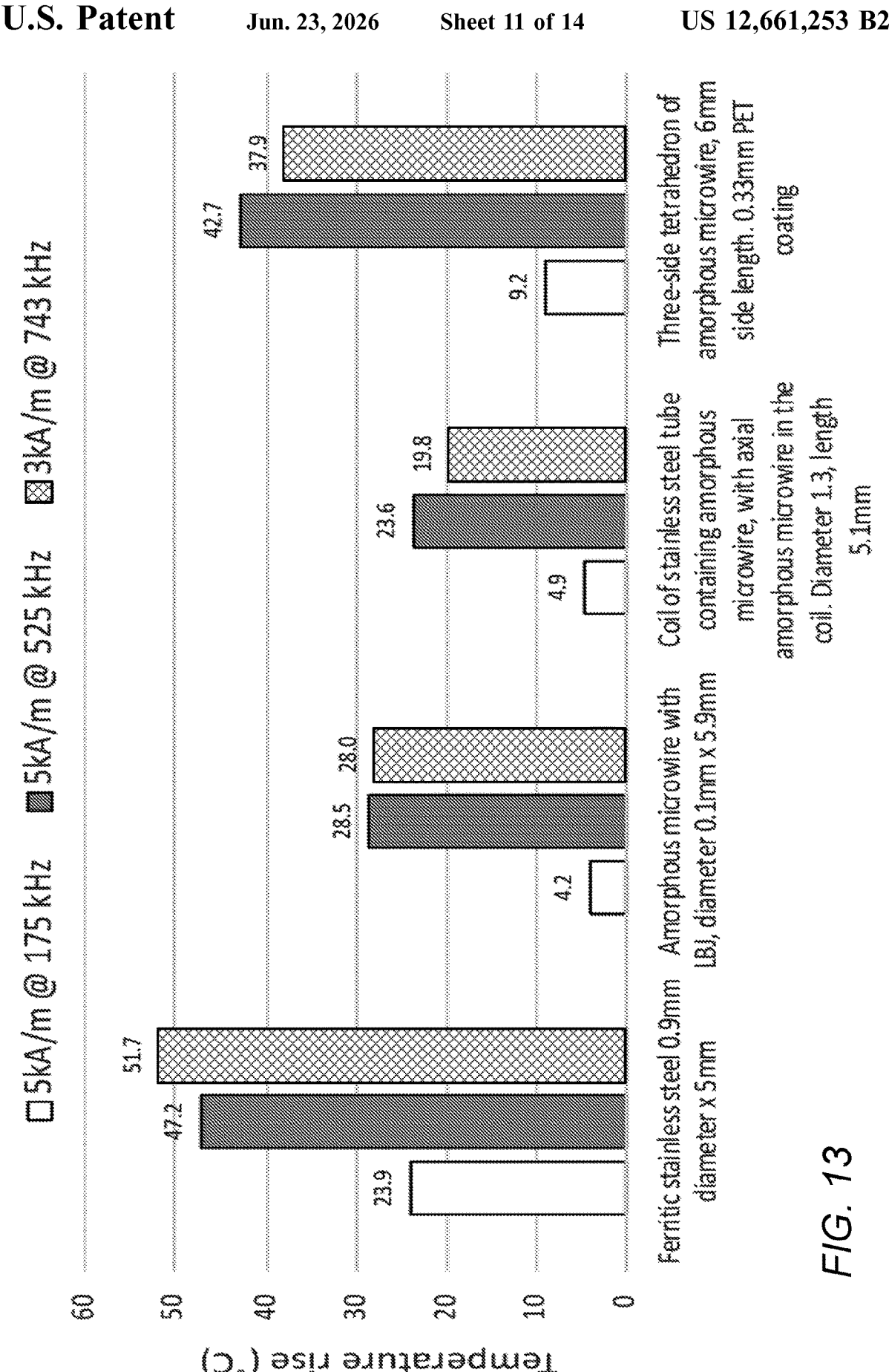
FIG. 13 is a graph illustrating heating effects of hyperthermia implants according to embodiments of the invention and other types of implant with different field strengths and frequencies.

FIG. 13 is a graph showing heating versus time for various magnetic hyperthermia implants, in particular a ferritic stainless steel marker ('a' in Example 1), an amorphous high permeability microwire with LBJ ('e' in Example 1), the marker of FIG. 8B comprising a coil implant of a LBJ microwire with an axial core piece of LBJ microwire, and a three-sided tetrahedron of amorphous LBJ microwire 60 with a PET coating 80 (as used in Example 4 and shown in FIG. 11B).

The graph shows that the heating effect increases with increasing field strength and with increasing frequency of the driving field.

EXAMPLE 8

Combined Magnetic Marker and Hyperthermia Implant for Locating and Heating a Treatment Area According to yet Another Embodiment of the Invention.

The implant as hereinbefore described has a significant added benefit of being able to dual-function as a marker, as described in the Applicant's co-pending unpublished Application No. GB1801224.5. The implant can also act as a magnetic marker that can be implanted for marking a target site in the body, such as a tumour or other lesion or site of interest in soft tissue and subsequently be detected and localised using a handheld probe (see FIG. 14A). The marker may be placed in or near a lesion or multiple markers may be placed to mark the margins or perimeter of a surgical site, for example the margins of a soft tissue sarcoma.

Figure 15:
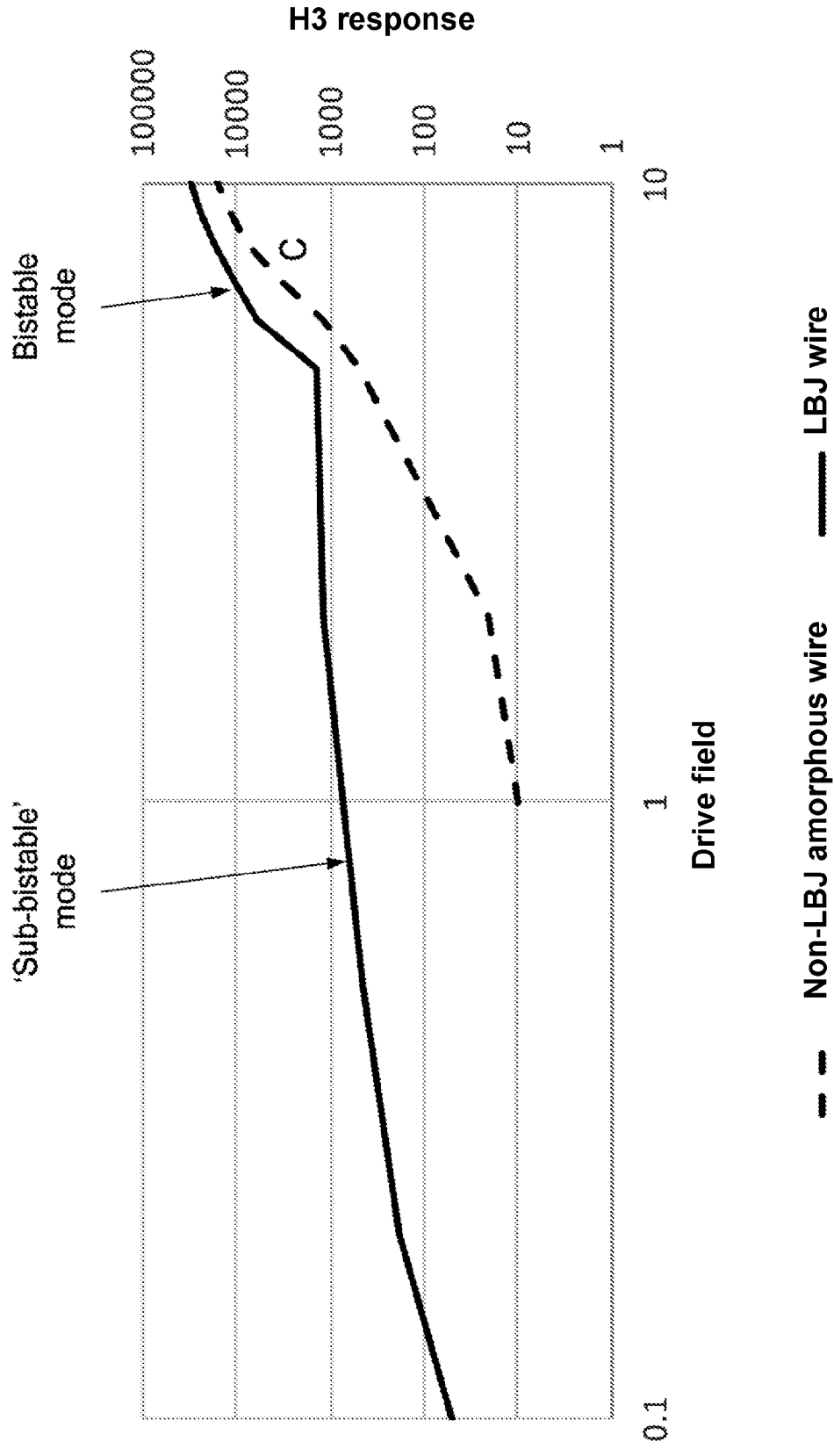
FIG. 15 shows a third harmonic (H3) response from a normal amorphous metal wire compared with a LBJ wire as excitation field is increased at 100 Hz.

The detection system for this type of marker utilises a different mode of excitation for LBJ materials that had not previously been recognised. The inventors found that a different mode of excitation for LBJ materials incorporated into the marker produced a measurable harmonic response even when the length of wire was below the 'critical length' and the excitation field was below the 'switching field', see FIG. 15. This was a previously unidentified "sub-bistable" behaviour in addition to the known bistable behaviour of LBJ materials. The concepts of 'critical length' and 'switching field' for LBJ wires are known from for example Vazquez (A soft magnetic wire for sensor applications., J. Phys. D: Appl. Phys. 29 (1996) 939-949). Furthermore, the effect increases in magnitude at higher excitation frequencies and can be operated at frequencies far higher than 3 kHz. This realisation has enabled a new type of detection system to be provided that has superior properties to previous systems that used implantable magnetic markers for marking the site of a lesion.

Thus this detection system employs an implantable magnetic marker comprising at least one piece of a large Barkhausen jump material (LBJ) which is deployed to mark a tissue site in the body for subsequent surgery, and a magnetic detection system including a drive coil to excite the marker. The system is characterised in that when the drive coil excites the marker with an alternating magnetic field below the switching field for bistable switching of the marker, a harmonic response is generated that allows the marker to be detected and localised. Furthermore, the field serves to heat the marker thereby simultaneously providing hyperthermia treatment of the site. Accordingly, the present invention provides a combined system for detecting the location of a tumour and providing hyperthermia treatment to this location using the same implant. This is clearly preferable to having to carry out multiple surgical procedures to insert and remove different types of implant for location of a treatment site and for carrying out hyperthermia treatment.

When the LBJ material is exposed to an external magnetic field whose field strength opposing the instantaneous magnetic polarization of said length of material exceeds a predetermined threshold value, the switching field $H_{SW}$, its magnetic polarization undergoes a rapid reversal. This reversal of magnetisation generates a magnetic pulse with rich harmonic components. Conventionally, the markers are sized to be above the so-called 'critical length', that is the length at which the magnetization can undergo the full bistable transition or 'flipping' behaviour which is required to generate a significant harmonic response. However, the 'sub-bistable' behaviour identified by the Applicant enables a harmonic response to be obtained from markers significantly below their critical length and/or below the switching field $H_{SW}$ and this is advantageous for use for localization of the implantable marker, as well as its use as a hyperthermia implant.

The harmonic approach also allows detection of the marker whilst being relatively impervious to sources of noise at the fundamental frequency such as stray fields, diamagnetic response from tissue, and Eddy currents.

A probe of the detection system is illustrated in FIG. 14B and contains one or more sense coils arranged to detect the changes in the magnetic field caused by the change in magnetisation of the marker, and ideally the probe gives the same magnitude of response regardless of the direction in which the marker is approached. This is to provide consistent feedback to a surgeon on the location of the marker relative to the probe.

A frequency generator for example an oscillator or waveform generator ($f_D$ is 0.5 to 30 kHz) generates a preferably sinusoidal alternating signal which excites one or more drive coils 102. A sinusoidal signal minimises the harmonic components in the drive field such that the sense coil detects no spurious harmonic signals. The one or more drive coils generate an alternating magnetic field that extends into the tissue containing a magnetic marker 6 comprising at least one piece of a large Barkhausen jump material (LBJ).

The alternating magnetic field excites the marker and the magnetisation of the marker leads to the generation of harmonic components in the field. Depending on the arrangement of the marker, the harmonics may be odd harmonics, ($3^{rd}$, $5^{th}$, $7^{th}$ etc.) or even harmonics ($2^{nd}$, $4^{th}$, $6^{th}$ etc.) or a combination of both odd and even harmonics. The marker is detected by measuring the magnitude of one or more of the harmonic frequencies directly or by measuring the ratio of the magnitude of one or more harmonics to others or to the magnitude of the fundamental frequency.

The response from the marker is detected by one or more sense coils to generate a sense voltage or current. Preferably the sense coils are in a handheld or robotic probe. A high-pass or notch filter may be arranged to filter out or attenuate at least components of the sense signal at the drive frequency so that the resulting signal has minimal content at the drive frequency and comprises higher harmonic components of the signal, for example the second, third, fourth, fifth or seventh order harmonics or combinations of these. The filter may take the form of a passive LCR type filter comprising a known arrangement of for example capacitors, inductors and resistors or an active filter comprising a known arrangement for example based on one or more op-amps.

The filtered signal may be fed to a harmonic detection circuit which amplifies one or more harmonic components of the signal and converts the signal to a measure of distance from the probe to the marker. A user display and sound generator provides a visual and audio output to the user indicating for example, the proximity of the marker or the magnitude of the magnetic signal. The system may indicate the proximity, size, distance to, direction or orientation of the marker, or combinations of these.

The drive signal from drive coils may be electronically filtered by filters to attenuate any harmonic parts of the drive signal so that the alternating magnetic field is primarily at the desired excitation or drive frequency. This helps to avoid spurious responses at higher frequencies that could be erroneously interpreted as harmonic responses. If desired, more than one drive frequency may be added to create a more complex magnetic signal, either by superposition/ modulation or by multiplexing the signals so that a different frequency is generated at different times.

As mentioned above, the hyperthermia implants of the present invention that may also serve as markers for a detection system comprise one or more lengths of material ("magnetic marker material") which gives a harmonic or non-linear response to an alternating magnetic field produced by a large Barkhausen discontinuity in the magnetisation curve. Examples of such materials include iron-, cobalt- and nickel-rich glass-coated amorphous microwires, iron-silicon-boron based amorphous microwires, iron-cobalt based amorphous microwires, and bulk metallic glass wires.

It is preferable to provide both a marker and a hyperthermia implant that provides a harmonic response to an alternating magnetic field that is uniform from any given direction. Various types of marker/implant are described in the Applicant's co-pending Application No. GB1801224.5 and include a length of magnetic marker material bent into a portion of a circle, with one end bent radially towards the centre and then bent substantially at 90° to form a portion along the axis of the circle, another may comprise lengths of magnetic marker material arranged along three orthogonal axes x, y and z to form the shape of a 'jack' or it may comprise a length of magnetic marker material in the shape of a circular standing wave, i.e. formed into a uniform wave shape and then bent round to join the ends and form a circle in plan view. However, it is to be appreciated that the implant is not limited to any one particular configuration.

The magnetic material of the implant may also be provided within a biocompatible barrier layer or shell. The shell may also function to assist in the deployment of the implant from an initial shape and configuration when it is inside a deployment device, to a final position once the implant has left the deployment device and is in the tissue. For example, the tube or tubes or shell containing the magnetic material may comprise a biocompatible shape memory alloy such as a Nitinol alloy, the alloy being manufactured such that on leaving the deployment device and being exposed to body temperature the material performs a shape transition and reconfigures from a pre-deployed shape that can fit within a narrow gauge needle e.g. 14 g-18 g to a final deployed shape.

In a further example, the tube or tubes containing the magnetic implant material comprises a biocompatible resiliently deformable material such as a superplastic Nitinol alloy or spring material, such that when it is deployed in the body it resiliently reconfigures through for example the elasticity of the material from a pre-deployed shape that can fit within a narrow gauge needle e.g. 14 g-18 g to a final deployed shape. A suitable deployment device may comprise a needle and a plunger. In use, the needle is inserted into the target tissue under imaging guidance. The deployment device is arranged such that on depression of the plunger, the magnetic implant is deployed from the end of the needle into the target tissue. The housing material may further be chosen to maximise Eddy current heating for example by using a more conductive material such as gold or a coating of gold.

The present invention provides a novel hyperthermia implant and system for hyperthermia treatment as well as a combined system for detecting the location of a treatment site and hyperthermically treating the site. The hyperthermia implant comprises at least a piece of LBJ magnetic material that is excited by a drive coil and effectively heats the surrounding tissue. The marker may be in the form of a coil of LBJ magnetic material or comprise one or more straight pieces of LBJ magnetic material or a combination of the two. The hyperthermia implant can also be excited at a field lower than the bistable switching field and the generated harmonics measured from any direction to determine the position and orientation of the implant, thereby providing its location. Where straight pieces of the LBJ magnetic material are used, these pieces of wire in the marker may also be provided below the critical length of the LBJ material required to enable bistable switching behaviour, e.g. below 10 mm and with a length to diameter ratio of less than 200.

The invention claimed is:

1. A hyperthermia system for heating an implant in a tissue of a body, the system comprising:

at least one drive coil arranged to excite the implant with an alternating magnetic field;

at least one microwire, wherein the at least one microwire is arranged in a three-edged or four-edged tetrahedral shape; and a magnetic field generator arranged to drive the alternating magnetic field or current through the at least one drive coil, the implant comprising a heat source provided by at least one piece of magnetic material provided in the implant, the magnetic material exhibiting a large Barkhausen jump (LBJ) in its magnetization curve, and wherein the implant is configured to provide a uniform heating output from the implant that is independent of the orientation of the implant relative to the direction of the alternating magnetic field, wherein excitation of the heat source at a frequency of 30-750 kHz provides hyperthermia treatment of a tissue surrounding the implant that is independent of an orientation of the implant with respect to a longitudinal axis of the alternating magnetic field.

2. The hyperthermia treatment system of claim 1 wherein the at least one drive coil excites the implant below a switching field required to initiate bistable switching behavior of the magnetic material exhibiting a LBJ.

3. The hyperthermia system of claim 1, wherein the implant comprises a coiled microwire.

4. The hyperthermia system of claim 3, wherein the implant further comprises a microwire arranged along a longitudinal axis of the coiled microwire or wherein the coiled microwire is arranged along an axis.

5. The hyperthermia treatment system of claim 1, further comprising the implant, wherein the implant has a length, wherein the length is greater than or equal to 2 mm.

6. A method of hyperthermia treatment comprising implanting a hyperthermia implant in tissue of a human or animal body, the implant comprising at least one piece of magnetic material that exhibits a large Barkhausen jump (LBJ) in its magnetisation curve; and exciting the implant with an alternating magnetic field to provide hyperthermia treatment to a tissue surrounding the implant, wherein the implant is configured to provide a magnitude of heating that is independent of an orientation of the implant with respect to a longitudinal axis of the alternating magnetic field.

7. A hyperthermia system for heating an implant when implanted in a tissue of a body, the system comprising:

the implant configured to generate a heat output when excited by a magnetic field, the implant comprising at least one magnetic microwire, the at least one magnetic microwire being formed of a large Barkhausen jump material, wherein the at least one magnetic microwire comprises a plurality of wire portions; and a magnetic field generator configured to generate the magnetic field having a direction of application, for exciting the implant in a sub-bistable mode;

wherein the plurality of wire portions are arranged with respect to one another such that during excitation, for all orientations of the implant with respect to the magnetic field, at least one of the wire portions defines an axis, which is angled by no more than 60° to the direction of application of the magnetic field, so that the implant provides a uniform heat output independent of its orientation.

8. The hyperthermia system of claim 7, wherein the implant further comprises a coiled microwire.

9. The hyperthermia system of claim 8, wherein the implant further comprises the at least one magnetic microwire arranged along a longitudinal axis of the coiled microwire.

10. The hyperthermia system of claim 7, wherein the at least one magnetic microwire is arranged in a three-edged or four-edged tetrahedral shape.

11. The hyperthermia system of claim 7, wherein the implant further comprises straight wire portions each having a length to diameter ratio of less than 100 or wherein one or more of the plurality of wire portions are straight wire portions each having a length to diameter ratio of less than 100.

12. The hyperthermia system of claim 11, wherein the straight wire portions each have a length of less than 25 mm, optionally less than 10 mm, or optionally less than 6 mm.

13. The hyperthermia system of claim 7, wherein the magnetic field generator is configured to generate the magnetic field at a frequency in the range 30-750 kHz.

14. The hyperthermia system of claim 13, wherein the magnetic field generator is configured to generate the magnetic field of a strength between 1000 A/m to 20,000 A/m at a frequency in the range 30-750 KHz.

15. The hyperthermia system of claim 7, wherein the at least one magnetic microwire comprises an iron-rich glass-coated amorphous microwire, a cobalt-rich glass-coated amorphous microwire, a nickel-rich glass-coated amorphous microwire, an iron-silicon-boron based amorphous microwire, an iron-based amorphous microwire, and/or a cobalt-based amorphous microwire.

16. The hyperthermia system of claim 7 further comprising a temperature sensor and a controller, the temperature sensor being arranged to sense a temperature of the implant and to output to the controller, and the controller being configured to adjust the strength of the magnetic field in dependence on the sensed temperature.

17. An implant for implanting in a tissue of a body, the implant comprising:

at least one magnetic microwire, the at least one magnetic microwire being formed of a large Barkhausen jump material;

wherein the implant is configured to generate a heat output when excited in a sub-bistable mode by a magnetic field having a direction of application; and wherein the at least one magnetic microwire comprises a plurality of wire portions;

and wherein the plurality of wire portions are arranged with respect to one another such that during excitation, for all orientations of the implant with respect to the magnetic field, at least one of the wire portions defines an axis, which is angled by 60° or less to the direction of application of the magnetic field, in order that the implant provides a uniform heat output independent of its orientation.

18. The implant of claim 17, wherein the at least one microwire comprises three microwires forming three edges of a tetrahedron or a three-legged tripod, or comprises four microwires forming four edges of a tetrahedron.

19. The implant of claim 17, wherein the implant comprises less than 2 mg of the large Barkhausen jump material.

20. A combined detection and hyperthermia system for locating and heating an implant when implanted in a tissue of a body, the combined system comprising:

the implant, wherein the implant has a length, wherein the length is greater than or equal to 2 mm;

a hyperthermia system comprising a magnetic field generator;

at least one sense coil arranged to detect a signal received from the implant; and at least one detector associated with the at least one sense coil, the at least one detector configured to detect a harmonic response from the implant, the magnetic field generator being configured to generate a first magnetic field at a first frequency between 1-100 kHz to excite the implant for locating the implant in the tissue, and to generate a second magnetic field at a second, higher, frequency between 30-750 kHz to excite the implant for providing the heat output, the magnetic field having a direction of application for exciting the implant in a sub-bistable mode.

* * * * *